United States Patent
Graziano et al.

(10) Patent No.: US 9,789,182 B2
(45) Date of Patent: Oct. 17, 2017

(54) COMBINATION OF ANTI-KIR AND ANTI-CTLA-4 ANTIBODIES TO TREAT CANCER

(71) Applicants: BRISTOL-MYERS SQUIBB COMPANY, Princeton, NJ (US); Innate Pharma, Marseilles (FR)

(72) Inventors: Robert F. Graziano, Frenchtown, NJ (US); Ashok K. Gupta, Clarksburg, MD (US); Su Young Kim, Belle Mead, NJ (US); Jon Wigginton, Collegeville, PA (US); Pascale Andre, Marseilles (FR)

(73) Assignees: BRISTOL-MYERS SQUIBB COMPANY, Princeton, NJ (US); INNATE PHARMA, Marseilles (FR)

( * ) Notice: Subject to any disclaimer, the term of this patent is extended or adjusted under 35 U.S.C. 154(b) by 32 days.

(21) Appl. No.: 14/437,029

(22) PCT Filed: Oct. 23, 2013

(86) PCT No.: PCT/US2013/066431
§ 371 (c)(1),
(2) Date: Apr. 20, 2015

(87) PCT Pub. No.: WO2014/066532
PCT Pub. Date: May 1, 2014

(65) Prior Publication Data
US 2015/0283234 A1 Oct. 8, 2015

Related U.S. Application Data

(60) Provisional application No. 61/717,304, filed on Oct. 23, 2012.

(51) Int. Cl.
*A61K 39/395* (2006.01)
*C07K 16/28* (2006.01)
*A61K 39/00* (2006.01)

(52) U.S. Cl.
CPC ...... *A61K 39/3955* (2013.01); *C07K 16/2803* (2013.01); *C07K 16/2818* (2013.01); *A61K 2039/507* (2013.01); *A61K 2039/545* (2013.01); *C07K 2317/565* (2013.01); *C07K 2317/92* (2013.01)

(58) Field of Classification Search
CPC ........ A61K 2039/507; A61K 2039/545; C07K 2317/565
USPC .................................... 424/139.1; 530/387.9
See application file for complete search history.

(56) References Cited

U.S. PATENT DOCUMENTS

2016/0123964 A1* 5/2016 Tumeh ............... G01N 33/5091
424/133.1
2016/0176962 A1* 6/2016 Murriel ............... A61K 31/282
424/136.1
2016/0185870 A1* 6/2016 Van Eenennaam
............... C07K 16/2803
424/133.1

FOREIGN PATENT DOCUMENTS

WO 2006072625 A2 7/2006
WO 2010014784 A2 2/2010

OTHER PUBLICATIONS

ClinicalTrials.gov (NCT01750580; pp. 1-4; Jan. 11, 2017).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Ascierto, Paolo, A., et al, "Anti-CTLA4 monoclonal antibodies: the past and the future in clinical application," Journal of Translational Medicine, Jan. 1, 2001, vol. 9, No. 196, pp. 1-5, XP055071066, ISSN: 1479-5876. DOI: 10.1186/1479-5876-8-38, the whole document.
Hodi, Stephen F. et al., "Improved Survival with Ipilimumab in Patients with Metastatic Melanoma," New England Journal of Medicine, Aug. 19, 2010, vol. 363, No. 8, pp. 711-723, XP-055015428, ISSN: 0028-4793, DOI: 10.1056/NEJMoaI003466, abstract.
International Search Report, PCT/US2013/066431, dated Feb. 14, 2014, pp. 1-5.
Rizvi, Naiyer, et al., "A Phase 1 Study of Lirilumab (BMS-986015), an Anti-KIR Monoclonal Antibody, Administered with Ipilimumab, an Anti-CTLA-4 Monoclonal Antibody, in Patients with Select Advanced Solid Tumors," May 31, 2013, pp. 1-1, XP-002718354, Retrieved from the Internet: URL:http://www.innate-pharma.com/sites/default/files/asco2013 tps3106 I.pdf <URL:http://www.innate-pharma.com/sites/default/files/asco2013%20tps3106%20I.pdf> [retrieved on Jan. 7, 2014], the whole document.
Romagne, Francois, et al., "Preclinical Characterization of 1-7F9, a novel human anti-KIR receptor therapeutic antibody that augments natural killer-mediated killing of tumor cells," Blood, American Society of Hematology, US, Sep. 24, 2009, vol. 114, No. 13, pp. 2667-2677, XP008120342, ISSN: 006-4971 DOI: 10.1182/BLOOD-2009-02-206532 [retrieved on Jun. 24, 2009],abstract.
International Search Report and Written Opinion, PCT/US2013/066431, dated Feb. 14, 2014, pp. 1-11.
International Preliminary Report on Patentability, PCT/US2013/066431, dated Apr. 28, 20154, pp. 1-7.

* cited by examiner

*Primary Examiner* — Lynn Bristol
(74) *Attorney, Agent, or Firm* — Nelson Mullins Riley & Scarborough LLP; Jane E. Remillard, Esq.; Jeanne M. DiGiorgio

(57) ABSTRACT

Provided are methods for clinical treatment of cancer (e.g., solid tumors or hematological malignancies) using an anti-KIR antibody in combination with an anti-CTLA-4 antibody.

15 Claims, 3 Drawing Sheets

COMBINATION OF ANTI-KIR AND ANTI-CTLA-4 ANTIBODIES TO TREAT CANCER

This application is a U.S. national stage filing of International Application No. PCT/US2013/066431, filed Oct. 23, 2013, which claims the benefit of U.S. Provisional Patent Application No. 61/717,304, filed Oct. 23, 2012, each of which is incorporated herein by reference in its entirety.

BACKGROUND

Natural killer (NK) cells constitute 15% of peripheral blood lymphocytes and play an important role in the ability of the innate immune system to fight off viral infections and also cancer (Purdy A K et al. (2009) *Cancer Biol Ther* 8:13-22). NK cells bind to target cells through multiple receptors, including natural cytotoxicity receptors (NCR), the Fc receptor CD 16, NKG2D, and others. Binding of ligand to receptor initiates tyrosine phosphorylation and recruitment of accessory signaling molecules. This cascade results in activation of the NK cell, release of preformed granules containing perforin and granzymes into the target cell, and apoptosis. The concurrent release of cytokines and chemokines results in a micro-environmental milieu that recruits other immune cells.

NK cells have the capability of binding every cell in the body (Murphy W J et al. (2012) *Biol Blood Marrow Transplant* 18:S2-S7). However, binding of normal cells does not result in cytotoxic activity because of the ability of NK cells to simultaneously utilize a different set of receptors to bind major histocompatibility complex (MHC) class I molecules. Binding of human leukocyte antigen (HLA) E to the NKG2A/CD94 heterodimeric receptor, or of HLA-A, B and C molecules to inhibitory killer Ig-like receptors (KIRs), results in tyrosine phosphorylation, recruitment of the signaling adaptors SHP-1 or SHP-2, and downstream signaling. The end result is a dominant signal that suppresses normal activation signals. Thus, KIR/HLA interaction can impact NK cell responsiveness and also the development of the total number of mature responsive NK cells, known as licensing.

There are seven inhibitory KIRs and seven activating KIRs, which is one factor that results in diversity of KIR inheritance and expression. KIR is also expressed on natural killer T (NKT) cells and a small subset of T cells (Uhrberg M et al. (2001) *J Immunol* 166:3923-3932). Thus, mechanistically, blockade of inhibitory KIR could induce anti-tumor effects by allowing for activation of NK cell and possibly also some T cells.

Evidence in support of NK cell involvement in the anti-tumor response comes from the hematopoietic stem cell transplant (HSCT) setting. Given the diversity in both KIR and HLA, it is not surprising that KIR on donor NK cells may not interact with host HLA, referred to as KIR mismatch. The finding that AML patients transplanted with KIR mismatched donor NK cells had lower relapse rates (3% versus 47%, p<0.01) and reduced risk of relapse (relative risk 0.48, 95% CI 0.29-0.78) gave scientific support for the role of NK cells in the anti-tumor response (Ruggeri L et al. (2007) *Blood* 110:433-440).

In melanoma, certain KIR and HLA combinations may provide a more immunosuppressive environment, since certain combinations are seen more frequently in metastatic patients compared to non-metastatic patients (Naumova E et al. (2005) *Cancer Immunol Immunother* 54:172-178). KIR mismatch has been shown to be a favorable prognostic marker for high risk neuroblastoma patients undergoing autologous HSCT (Delgado D C et al. (2010) *Cancer Res* 70:9554-9561).

Experimental support for the important role of NK cells in solid tumors comes from murine studies in which mice lacking T cells could still eradicate large solid tumors following NK cell activation by the addition of IL-15 (Liu R B et al. (2012) *Cancer Res* 72:1964-1974).

Full activation of naive T cells requires stimulation of the antigen receptor by peptide-major histocompatibility complexes and by co-stimulatory signals. These signals are provided by the engagement of CD28, which is constitutively expressed on T cell surfaces, with CD80 (B7.1) and CD86 (B7.2) molecules, which are present on antigen presenting cells (APCs). Cytotoxic T lymphocyte antigen 4 (CTLA-4; CD152) is an activation-induced T cell surface molecule that also binds to CD80 and CD86, but with greater avidity than CD28. CTLA-4 ligation down-regulates T cell responses, which results in abrogation of the effects provided by T cell activation. The blockade of CTLA-4 interaction with CD80/86 results in increased T cell activation. Ipilimumab (Yervoy®) is a fully human IgG1κ monoclonal antibody targeting CTLA-4 that inhibits the negative downstream signaling that occurs when CTLA-4 engages its ligands, CD80 and CD86, on APCs. As a result, activated T cells are able to maintain their CD28 mediated signaling resulting in IL-2 secretion and proliferation of CD8 T cells in response to an antigen.

Ipilimumab is currently approved for the treatment of metastatic melanoma, for which it has shown an overall survival advantage (Hodi FS et al. (2010) *N Engl J Med* 363:711-723). Administration of 4 doses of ipilimumab alone or in combination with a gp100 peptide vaccine improved survival by 4 months compared with the administration of gp100 vaccine alone in subjects with metastatic melanoma who had progressed after chemotherapy or IL-2 therapy.

Patients with metastatic or refractory tumors have very poor prognosis (Rosenberg S A et al. (2011) *Cancer immunotherapy in Cancer: Principles & Practice of Oncology* (Eds. DeVita V T, Lawrence T S and Rosenberg S A) 332-344 (Lippincott Williams & Wilkins, Philadelphia Pa.)). Despite advances in multimodal therapy, increases in overall survival in this patient population have been limited.

Accordingly, it is an object of the present invention to provide improved methods for treating subjects with such tumors (e.g., advanced solid tumors).

SUMMARY

Provided herein are methods for treating cancer, e.g., advanced solid tumors or hematological malignancies, in a human patient, comprising administering to the patient a combination of an anti-KIR antibody and an anti-CTLA-4 antibody, wherein the combination is administered (or is for administration) according to a particular clinical dosage regimen (i.e., at a particular dose amount and according to a specific dosing schedule). In one embodiment, the human patient suffers from non-small cell lung cancer (NSCLC), castrate resistant prostate cancer (CRPC) or melanoma.

An exemplary anti-KIR antibody is lirilumab (also known as BMS-986015 or IPH2102) comprising the heavy and light chains having the sequences shown in SEQ ID NOs:1 and 2, respectively, or antigen binding fragments and variants thereof. In other embodiments, the antibody comprises the heavy and light chain complementarity determining regions (CDRs) or variable regions (VRs) of lirilumab.

Accordingly, in one embodiment, the antibody comprises the CDR1, CDR2, and CDR3 domains of the heavy chain variable (VH) region of lirilumab having the sequence shown in SEQ ID NO:3, and the CDR1, CDR2 and CDR3 domains of the light chain variable (VL) region of lirilumab having the sequence shown in SEQ ID NO:5. In another embodiment, the antibody comprises CDR1, CDR2 and CDR3 heavy chain sequences set forth in SEQ ID NOs:7, 8, and 9, respectively, and CDR1, CDR2 and CDR3 light chain sequences as set forth in SEQ ID NOs:10, 11, and 12, respectively. In another embodiment, the antibody comprises VH and/or VL regions having the amino acid sequences set forth in SEQ ID NO:3 and/or SEQ ID NO:5, respectively. In another embodiment, the antibody comprises the VH and/or VL regions encoded by the nucleic acid sequences set forth in SEQ ID NO:4 and/or SEQ ID NO:6, respectively. In another embodiment, the antibody competes for binding with, and/or binds to the same epitope on KIR as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

An exemplary anti-CTLA-4 antibody is ipilimumab (also known as 10D1, MDX-010, MDX-101, and Yervoy®) comprising heavy and light chains having the sequences shown in SEQ ID NOs:17 and 18, respectively, or antigen binding fragments and variants thereof (see, e.g., WO01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab having the sequence shown in SEQ ID NO:19, and the CDR1, CDR2 and CDR3 domains of the VL region of ipilimumab having the sequence shown in SEQ ID NO:20. In another embodiment, the antibody comprises the heavy chain CDR1, CDR2 and CDR3 domains having the sequences set forth in SEQ ID NOs:21, 22, and 23, respectively, and the CDR1, CDR2 and CDR3 domains having the sequences set forth in SEQ ID NOs: 24, 25, and 26, respectively. In another embodiment, the antibody comprises VH and/or VL regions having the amino acid sequences set forth in SEQ ID NO:19 and/or SEQ ID NO:20, respectively. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with SEQ ID NO:19 or SEQ ID NO:20).

Accordingly, in one aspect, methods of treating solid tumors (e.g., advanced solid tumors) in a human patient are provided, the methods the method comprising: administering to the patient, an effective amount of each of:

(a) an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, and (b) an anti-CTLA-4 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:20, wherein the anti-KIR antibody and anti-CTLA-4 antibody are first administered in combination (A) every 3 weeks for a total of 4 doses over 12 weeks during an induction phase, followed by (B) every 12 weeks for 4 doses starting at week 24 during a maintenance phase, and wherein the anti-KIR antibody is administered at a dose of 0.1-20 mg/kg body weight and the anti-CTLA-4 antibody is administered at a dose of 0.1-20 mg/kg body weight during both the induction and maintenance phases.

In certain embodiments, each dose of the anti-KIR antibody is administered at 0.1, 0.3, 1, 3, 5 or 10 mg/kg. In preferred embodiments, each dose of the anti-KIR antibody is administered at 0.3, 1 or 3 mg/kg.

In other embodiments, each dose of the anti-CTLA-4 antibody is administered at 0.1, 0.3, 1, 3, 5 or 10 mg/kg body weight. In preferred embodiments, each dose of the anti-CTLA-4 antibody is administered at 1, 3 or 10 mg/kg. In more preferred embodiments, the anti-CTLA-4 antibody is administered at a dose of 3 mg/kg.

In one embodiment, the anti-KIR antibody and anti-CTLA-4 antibody are administered at the following doses during either the induction or maintenance phase:

(a) 0.1 mg/kg anti-KIR antibody and 3 mg/kg of anti-CTLA-4 antibody;

(b) 0.3 mg/kg anti-KIR antibody and 3 mg/kg of anti-CTLA-4 antibody;

(c) 1 mg/kg anti-KIR antibody and 3 mg/kg of anti-CTLA-4 antibody;

(d) 3 mg/kg anti-KIR antibody and 3 mg/kg of anti-CTLA-4 antibody;

(e) 3 mg/kg anti-KIR antibody and 10 mg/kg of anti-CTLA-4 antibody; or (f) 10 mg/kg anti-KIR antibody and 10 mg/kg of anti-CTLA-4 antibody.

Accordingly, in certain embodiments, the doses of the anti-KIR and/or anti-CTLA-4 antibody are calculated in mg of antibody per kg body weight of patient (mg/kg). However, in other embodiments, the dose of the anti-KIR and/or anti-PD-1 antibody is a flat-fixed dose that is fixed irrespective of the weight of the patient. For example, the anti-KIR and/or anti-CTLA-4 antibody may be administered at a fixed dose of 5, 20, 75, 200, 400, 750 or 1500 mg, without regard to the patient's weight. In certain embodiments, the administered dose of the anti-CTLA-4 antibody may be fixed at 200 or 750 mg, while the anti-KIR antibody is administered at a fixed dose of 5, 20, 75, 200, 400 or 750 mg. In another embodiment, dosage regimens are adjusted to provide the optimum desired response (e.g., an effective response).

In other embodiments, the anti-KIR and/or anti-CTLA-4 antibodies are administered on (1) day 1, week 1, (2) day 22, week 4, (3) day 43, week 7, and (4) day 64, week 10 of the induction phase. In another embodiment, the induction phase ends on day 84 of week 12. In another embodiment, the anti-KIR and anti-CTLA-4 antibodies are administered on day 1 of week 24, day 1 of week 36, day 1 of week 48, and day 1 of week 60 of the maintenance phase.

In one embodiment, the anti-PD-1 antibody and anti-CTLA-4 antibody are administered as a first ("front") line of treatment (e.g., the initial or first treatment). In another embodiment, the anti-PD-1 antibody and anti-CTLA-4 antibody are administered as a second line of treatment (e.g., after initial treatment with the same or a different therapeutic, including after relapse and/or where the first treatment has failed).

The anti-KIR and anti-CTLA-4 antibodies described herein can be administered to a subject by any suitable means. In one embodiment, the antibodies are formulated for intravenous administration. In another embodiment, the antibodies are administered simultaneously (e.g., in a single formulation or concurrently as separate formulations). Alternatively, in another embodiment, the antibodies are administered sequentially (e.g., as separate formulations).

The efficacy of the treatment methods provided herein can be assessed using any suitable means. In one embodiment, the treatment produces at least one therapeutic effect selected from the group consisting of reduction in size of a tumor, reduction in number of metastasic lesions over time, complete response, partial response, and stable disease.

Also provided are kits that include a pharmaceutical composition containing an anti-KIR antibody, such as lirilumab, and an anti-CTLA-4 antibody, such as ipilimumab, and a pharmaceutically-acceptable carrier, in a therapeutically effective amount adapted for use in the methods described herein. In one embodiment, the kit comprises:

(a) a dose of an anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5;

(b) a dose of an anti-CTLA-4 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:20, (c) instructions for using the anti-KIR antibody and anti-CTLA-4 antibody in the methods of the invention.

In another aspect, an anti-KIR antibody is provided, the anti-KIR antibody comprising the CDR1, CDR2 and CDR3 domains in a heavy chain variable region having the sequence set forth in SEQ ID NO:3, and the CDR1, CDR2 and CDR3 domains in a light chain variable region having the sequence set forth in SEQ ID NO:5, for co-administration with an anti-CTLA-4 antibody comprising the CDR1, CDR2 and CDR3 domains in a heavy chain variable region having the sequence set forth in SEQ ID NO:19, and the CDR1, CDR2 and CDR3 domains in a light chain variable region having the sequence set forth in SEQ ID NO:20, wherein the anti-KIR antibody and anti-CTLA-4 antibody are first administered in combination (A) every 3 weeks for a total of 4 doses over 12 weeks during an induction phase, followed by (B) every 12 weeks for 4 doses starting at week 24 during a maintenance phase, and wherein the anti-KIR antibody is administered at a dose of 0.1, 0.3, 1, or 3 mg/kg and the anti-CTLA-4 antibody is administered at a dose of 3 or 10 mg/kg during both phases.

In another aspect of the invention, the anti-CTLA-4 antibody in any of the aforementioned embodiments is replaced by, or combined with, an immunoregulatory checkpoint inhibitor, for example an inhibitor of the PD-1 pathway such as an anti-PD-1, anti-PD-L1 or anti-PD-L2 antibody. Exemplary anti-PD-1 antibodies are described in WO 2006/121168, WO 2008/156712, WO 2012/145493, WO 2009/014708 and WO 2009/114335, the teachings of which are hereby incorporated into this application by reference. Exemplary anti-PD-L1 antibodies are described in WO 2007/005874, WO 2010/077634 and WO 2011/066389, and exemplary anti-PD-L2 antibodies are described in WO 2004/007679, the teachings of all of which are hereby incorporated by reference, Accordingly, the invention also features methods, compositions and kits for treating cancer in human patients using the above-described clinically effective dosages of an anti-KIR antibody combined with the above-described clinically effective dosages of an anti-CTLA-4 antibody, wherein the dosage of the anti-CTLA-4 antibody is replaced by the same dosage of an anti-PD-1, anti-PD-L1 or anti-PD-L2 antibody.

DETAILED DESCRIPTION

I. Definitions

Figure 1:
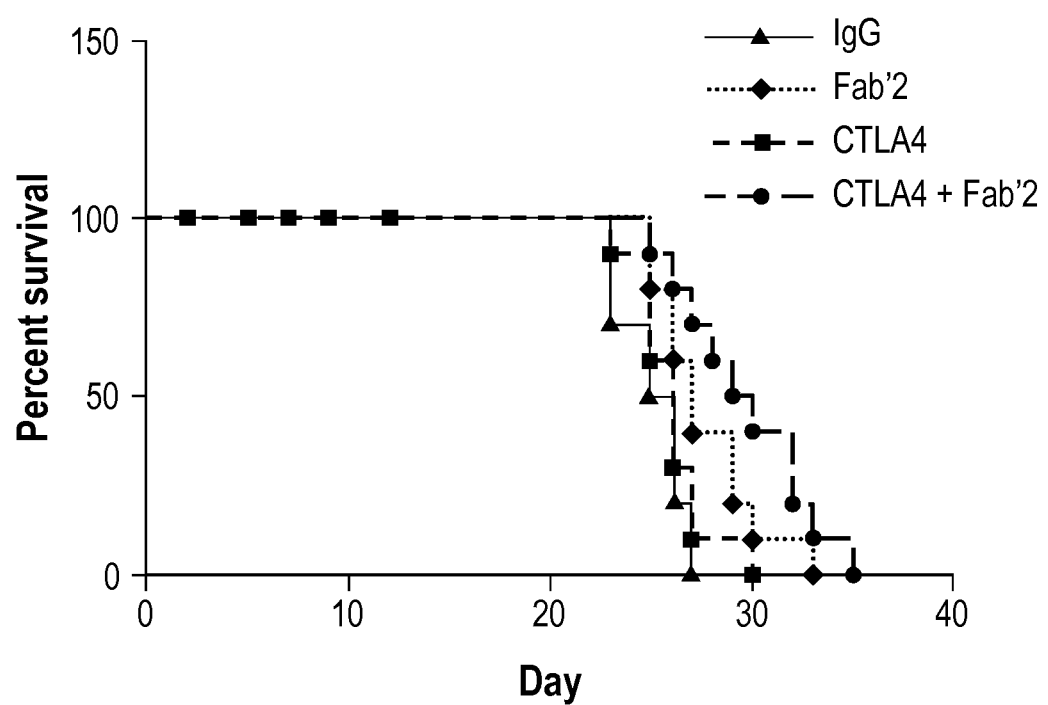
FIG. 1 shows the anti-tumor efficacy of anti-KIR and anti-CTLA-4 antibodies in a murine acute myeloid leukemia (AML) model.

As used herein, the term "subject" or "patient" is a human cancer patient (e.g., a patient having an advanced solid tumor, such as an advanced refractory solid tumor).

As used herein, "cancer" is a term used for diseases in which abnormal cells divide without control and are able to invade other tissues. Cancers include solid tumors and hematological tumors.

Solid tumors are neoplasms (new growth of cells) or lesions (damage of anatomic structures or disturbance of physiological functions) formed by an abnormal growth of body tissue cells other than blood, bone marrow or lymphatic cells. A solid tumor consists of an abnormal mass of cells, which may stem from different tissue types such as liver, colon, breast, or lung, and which initially grows in the organ of its cellular origin. However, solid tumors may spread to other organs through metastatic tumor growth in advanced stages of the disease.

Hematological tumors are cancer types affecting the blood, bone marrow, and lymph nodes. Hematological tumors can derive from either of the two major blood cell lineages, i.e., myeloid and lymphoid cell lines. The myeloid cell line normally produces granulocytes, erythrocytes, thrombocytes, macrophages, and mast cells, whereas the lymphoid cell line produces B, T, NK and plasma cells. Lymphomas (e.g., Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin.

As used herein, an "advanced" cancer is a cancer that has migrated from its original site to other areas of the body. In some cases, it is locally advanced in a vital organ, but has not reached distant sites. In other cases, the cancer may have metastasized or spread throughout the body through the lymph system or bloodstream.

As used herein, a "refractory cancer" (also known as a "resistant" cancer) is a cancer that does not respond to treatment (e.g., the cancer may be resistant at the beginning of treatment or it becomes resistant during treatment). In one embodiment, the cancer is a refractory cancer that does not respond to anti-KIR therapy, anti-CTLA-4 therapy, or standard therapy. As used herein, a "non-responder" is a subject who does not respond to treatment. A "responder" is a subject who responds to treatment (e.g., demonstrates some beneficial effect in response to treatment, such as amelioration of at least one symptom of a disease or disorder).

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of solid tumor. Effective treatment may refer to alleviation of at least one symptom of a solid tumor. Such effective treatment may, e.g., reduce patient pain, reduce the size and/or number of lesions, may reduce or prevent metastasis of a tumor, and/or may slow tumor growth.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of anti-KIR antibody and the amount of anti-CTLA-4 antibody, in combination, clinically proven to effect a significant decrease in cancer or slowing of progression of cancer, such as an advanced solid tumor.

As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent (e.g., the anti-KIR antibody and/or anti-CTLA-4 antibody).

As used herein, a "body surface area (BSA)-based dose" refers to a dose (e.g., of the anti-KIR antibody and/or anti-CTLA-4 antibody) that is adjusted to the body-surface area (BSA) of the individual patient. A BSA-based dose may be provided as mg/kg body weight. Various calculations have been published to arrive at the BSA without direct measurement, the most widely used of which is the Du Bois formula (see Du Bois D and Du Bois E F (1916) *Arch Internal Med* 17 (6):863-71; Verbraecken J et al. (2006) *Metabolism—Clinical and Experimental* 55 (4):515-24). Other exemplary BSA formulas include the Mosteller formula (Mosteller R D (1987) *N Engl J Med* 317:1098), the Haycock formula (Haycock G B et al. (1978) *J Pediatr* 93:62-66), the Gehan and George formula (Gehan E A and George S L (1970) *Cancer Chemother Rep* 54:225-235), the Boyd formula (Current J D (1998) *The Internet Journal of Anesthesiology* 2 (2); and Boyd, E (1935) University of Minnesota. The Institute of Child Welfare, Monograph Series, No. x. London: Oxford University Press), the Fujimoto formula (Fujimoto S et al. (1968) *Nippon Eiseigaku Zasshi* 5:443-50), the Takahira formula (Fujimoto S et al. (1968) *Nippon Eiseigaku Zasshi* 5:443-50), and the Schlich formula (Schlich E et al. (2010) *Ernährungs Umschau* 57:178-183).

The term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

As used herein, the terms "induction" and "induction phase" are used interchangeably and refer to the first phase of treatment in the clinical trial. For example, during induction, subjects may receive intravenous doses of an anti-KIR antibody (e.g., lirilumab) in combination with an anti-CLTA-4 antibody (e.g., ipilimumab) every 3 weeks for a total of 4 doses.

As used herein, the terms "maintenance" and "maintenance phase" are used interchangeably and refer to the second phase of treatment in the clinical trial. For example, during maintenance, subjects may receive an anti-KIR antibody (e.g., lirilumab) in combination with an anti-CLTA-4 antibody (e.g., ipilimumab) therapy every 12 weeks for an additional 4 doses starting at week 24. In certain embodiments, treatment is continued as long as clinical benefit is observed or until unmanageable toxicity or disease progression occurs.

As used herein, a "Killer Ig-like Receptor", "Killer Inhibitory Receptor", or "KIR", refers to a protein or polypeptide encoded by a gene that is a member of the KIR gene family or by a cDNA prepared from such a gene. A detailed review of the KIR gene family, including the nomenclature of KIR genes and KIR gene products, and Genbank accession numbers for exemplary KIRs, is "The KIR Gene Cluster" by M. Carrington and P. Norman, available at the NCBI website called "Bookshelf" (accessible via the World-Wide Web (WWW) address ncbi.nlm.nih.gov/books). The sequences of human KIR genes and cDNAs, as well as their protein products, are available in public databases, including GenBank. Non-limiting exemplary GenBank entries of human KIRs have the following accession numbers: KIR2DL1: Genbank accession number U24076, NM_014218, AAR16197, or L41267; KIR2DL2: Genbank accession number U24075 or L76669; KIR2DL3: Genbank accession number U24074 or L41268; KIR2DL4: Genbank accession number X97229; KIR2DS1: Genbank accession number X89892; KIR2DS2: Genbank accession number L76667; KIR2DS3: Genbank accession number NM_012312 or L76670 (splice variant); KIR3DL1: Genbank accession number L41269; and KIR2DS4: Genbank accession number AAR26325. A KIR may comprise from 1 to 3 extracellular domains, and may have a long (i.e., more than 40 amino acids) or short (i.e., less than 40 amino acids) cytoplasmic tail. As previously described herein, these features determine the nomenclature of a KIR. Exemplary KIR2DL1, KIR2DL2, KIR2DL3, and KIR2DS4 molecules comprise polypeptides having the following respective amino acid sequences:

KIR2DL1 extracellular domain:
HEGVHRKPSLLAHPGXLVKSEETVILQCWSDVMFEHFLLHREGMFNDTLR

LIGEHHDGVSKANFSISRMTQDLAGTYRCYGSVTHSPYQVSAPSDPLDIV

IIGLYEKPSLSAQXGPTVLAGENVTLSCSSRSSYDMYHLSREGEAHERRL

PAGPKVNGTFQADFPLGPATHGGTYRCFGSFHDSPYEWSKSSDPLLVSVT

GNPSNSWPSPTEPSSKTGNPRHLH (SEQ ID NO: 13), where

"X" at position 16 is P or R, and where "X" at position 114 is P or L, representing allelic variants.

KIR2DL2 extracellular domain:
(SEQ ID NO: 14)
HEGVHRKPSLLAHPGRLVKSEETVILQCWSDVRFEHFLLHREGKFKDTLH

LIGEHHDGVSKANFSIGPMMQDLAGTYRCYGSVTHSPYQLSAPSDPLDIV

ITGLYEKPSLSAQPGPTVLAGESVTLSCSSRSSYDMYHLSREGEAHECRF

SAGPKVNGTFQADFPLGPATHGGTYRCFGSFRDSPYEWSNSSDPLLVSVI

GNPSNSWPSPTEPSSKTGNPRHLH

KIR2DL3 extracellular domain:
(SEQ ID NO: 15)
HEGVHRKPSLLAHPGPLVKSEETVILQCWSDVRFQHFLLHREGKFKDTLH

LIGEHHDGVSKANFSIGPMMQDLAGTYRCYGSVTHSPYQLSAPSDPLDIV

ITGLYEKPSLSAQPGPTVLAGESVTLSCSSRSSYDMYHLSREGEAHERRF

SAGPKVNGTFQADFPLGPATHGGTYRCFGSFRDSPYEWSNSSDPLLVSVT

GNPSNSWPSPTEPSSETGNPRHLH

KIR2DS4 extracellular domain:
(SEQ ID NO: 16)
QEGVHRKPSFLALPGHLVKSEETVILQCWSDVMFEHFLLHREGKFNNTLH

LIGEHHDGVSKANFSIGPMMPVLAGTYRCYGSVPHSPYQLSAPSDPLDMV

The term "KIR2DL2/3" refers to either or both of the KIR2DL2 and KIR2DL3 receptors. These two receptors have a very high homology, are encoded by allelic forms of the same gene, and are considered by the art to be functionally similar.

As used herein, the terms "Cytotoxic T Lymphocyte-Associated Antigen-4", "Cytotoxic T Lymphocyte-Antigen-4", "CTLA-4", "CTLA-4", "CTLA-4 antigen" and "CD152" (see, e.g., Murate (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32).

CTLA-4 is a protein receptor that downregulates the immune system. CTLA-4 is found on the surface of T cells, which lead the cellular immune attack on antigens. The T cell attack can be turned on by stimulating the CD28 receptor on the T cell. The T cell attack can be turned off by stimulating the CTLA-4 receptor, which acts as an "off" switch.

The complete cDNA sequence of human CTLA-4 has the Genbank accession number L15006. The region of amino acids 1-37 is the leader peptide; 38-161 is the extracellular V-like domain; 162-187 is the transmembrane domain; and 188-223 is the cytoplasmic domain. Variants of the nucleotide sequences have been reported, including a G to A transition at position 49, a C to T transition at position 272, and an A to G transition at position 439. The amino acid sequence of human CTLA-4 is set forth in Genbank accession number AAL07473.1 (SEQ ID NO:27).

IIa. Anti-KIR Antibodies

Anti-human-KIR antibodies (or VH/VL domains derived therefrom) suitable for use in the invention can be generated using methods well known in the art. Alternatively, art recognized anti-KIR antibodies can be used. In preferred embodiments, the anti-KIR antibody is cross-reactive with multiple inhibitory KIR receptors and potentiates the cytotoxicity of NK cells bearing one or more of these receptors. For example, the anti-KIR antibody may bind to each of KIR2D2DL1, KIR2DL2, and KIR2DL3, and potentiate NK cell activity by reducing, neutralizing and/or reversing inhibition of NK cell cytotoxicity mediated by any or all of these KIRs. In further embodiments, the anti-KIR antibody does not bind KIR2DS4 and/or KIR2DS3. For example, monoclonal antibodies 1-7F9 (also known as IPH2101), 14F1, 1-6F1 and 1-6F5, described in WO 2006/003179, the teachings of which are hereby incorporated by reference, can be used. Antibodies that compete with any of these art-recognized antibodies for binding to KIR also can be used. Additional art-recognized anti-KIR antibodies which can be used include, for example, those disclosed in WO 2005/003168, WO 2005/009465, WO 2006/072625, WO 2006/072626, WO 2007/042573, WO 2008/084106, WO 2010/065939, WO 2012/071411 and WO/2012/160448.

An exemplary anti-KIR antibody is lirilumab (also known as BMS-986015 or IPH2102) comprising heavy and light chains having the sequences shown in SEQ ID NOs:1 and 2, respectively, or antigen binding fragments and variants thereof. Lirilumab is a fully human anti-KIR antibody that comprises the same heavy and light chain variable regions as 1-7F9 (described in WO 2006/003179), and thus binds to the same epitope as 1-7F9, but differs from 1-7F9 in that (1) it is prepared in Chinese hamster ovary (CHO) cells, whereas 1-7F9 is prepared from hybridoma cells, and (2) a stabilizing hinge mutation (S231P) has been introduced into lirilumab (WO 2008/084106).

In other embodiments, the antibody comprises the heavy and light chain CDRs or variable regions of lirilumab. Accordingly, in one embodiment, the antibody comprises the CDR1, CDR2, and CDR3 domains of the VH region of lirilumab having the sequence set forth in SEQ ID NO:3, and the CDR1, CDR2 and CDR3 domains of the VL region of lirilumab having the sequence set forth in SEQ ID NO:5. In another embodiment, the antibody comprises heavy chain CDR1, CDR2 and CDR3 domains having the sequences set forth in SEQ ID NOs:7, 8, and 9, respectively, and light chain CDR1, CDR2 and CDR3 domains having the sequences set forth in SEQ ID NOs:10, 11, and 12, respectively. In another embodiment, the antibody comprises VH and/or VL regions having the amino acid sequences set forth in SEQ ID NO:3 and/or SEQ ID NO: 5, respectively. In another embodiment, the antibody comprises the heavy chain variable (VH) and/or light chain variable (VL) regions encoded by the nucleic acid sequences set forth in SEQ ID NO:4 and/or SEQ ID NO:6, respectively. In another embodiment, the antibody competes for binding with, and/or binds to the same epitope on KIR as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

IIb. Anti-CTLA-4 Antibodies

Anti-human-CTLA-4 antibodies (or VH and/or VL domains derived therefrom) suitable for use in the invention can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) *Proc Natl Acad Sci USA* 95(17):10067-10071; Camacho et al. (2004) *J Clin Oncology* 22(145): Abstract No. 2505 (antibody CP-675206); and Mokyr et al. (1998) *Cancer Res* 58:5301-5304 can be used in the methods disclosed herein. The teachings of each of the aforementioned publications are hereby incorporated by reference. Antibodies that compete with any of these art-recognized antibodies for binding to CTLA-4 also can be used.

An exemplary anti-CTLA-4 antibody is ipilimumab comprising heavy and light chains having the sequences set forth in SEQ ID NOs:17 and 18, respectively, or antigen binding fragments and variants thereof (see WO 01/14424). In other embodiments, the antibody comprises the heavy and light chain CDRs or variable regions of ipilimumab. Accordingly, in one embodiment, the antibody comprises the CDR1, CDR2, and CDR3 domains of the VH region of ipilimumab having the sequence set forth in SEQ ID NO:19, and the CDR1, CDR2 and CDR3 domains of the VL region of ipilimumab having the sequence shown in SEQ ID NO:20. In another embodiment, the antibody comprises the heavy chain CDR1, CDR2 and CDR3 domains having the sequences set forth in SEQ ID NOs:21, 22, and 23, respectively, and the CDR1, CDR2 and CDR3 domains having the sequences set forth in 24, 25, and 26, respectively. In another embodiment, the antibody comprises VH and/or VL regions having the amino acid sequences set forth in SEQ ID NO:19 and/or SEQ ID NO:20, respectively. In another embodiment, the antibody competes for binding with, and/or binds to the same epitope on CTLA-4 as, the above-mentioned antibodies. In another embodiment, the antibody has at least about 90% variable region amino acid sequence identity with the above-mentioned antibodies (e.g., at least about 90%, 95%, or 99% variable region identity with SEQ ID NO:19 or SEQ ID NO:20).

III. Pharmaceutical Compositions

Pharmaceutical compositions suitable for administration to a patient are typically in forms suitable for parenteral administration, e.g., in a liquid carrier, or suitable for reconstitution into liquid solution or suspension, for intravenous administration.

In general, compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions (e.g., comprising an anti-KIR and/or CTLA-4 antibody). Liquid compositions for parenteral administration can be formulated for administration by injection or continuous infusion. Routes of administration by injection or infusion include intravenous, intraperitoneal, intramuscular, intrathecal and subcutaneous. In one embodiment, the anti-KIR and/or anti-CTLA-4 antibodies are administered intravenously (e.g., separately or together, each, e.g., over the course of 30 minutes, one hour, 90 minutes, or two hours).

IV. Patient Populations

Provided herein are methods effective for treating cancer (e.g., solid tumors or hematological malignancies) in a human patient using a combination of an anti-KIR antibody and an anti-CTLA-4 antibody.

Because these methods operate by enhancing an immune response via blockade of inhibitory receptors on T cells and NK cells, they are applicable to a very broad range of cancers. In one embodiment, the human patient suffers from non-small cell lung cancer (NSCLC), castrate resistant prostate cancer (CRPC) or melanoma. Examples of additional cancers that may be treated using a combination of an anti-CTLA-4 antibody and an anti-KIR antibody include liver cancer, bone cancer, pancreatic cancer, skin cancer, cancer of the head or neck, breast cancer, lung cancer, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers.

Patients can be tested or selected for one or more of the above described clinical attributes prior to, during or after treatment.

V. Combination Therapy

Combination therapies provided herein involve administration of an anti-KIR antibody and another antibody that blocks an inhibitory immune receptor (e.g., a receptor, which upon binding to its natural ligand, inhibits/neutralizes activity, such as cytotoxic activity), such as an anti-CTLA-4 antibody, to treat subjects afflicted with cancer (e.g., advanced solid tumors or blood cancers).

In one embodiment, the invention provides an anti-KIR antibody and an anti-CTLA-4 antibody in combination to treat subjects having a solid tumor (e.g., an advanced solid tumor). In another embodiment, the combination is used to treat subjects having a hematological malignancy. In one embodiment, the anti-KIR antibody is lirilumab. In another embodiment, the anti-CTLA-4 antibody is ipilimumab.

As used herein, adjunctive or combined administration (coadministration) includes simultaneous administration of the compounds in the same or different dosage form, or separate administration of the compounds (e.g., sequential administration). Thus, the anti-KIR and anti-CTLA-4 antibodies can be simultaneously administered in a single formulation. Alternatively, the anti-KIR and anti-CTLA-4 antibodies can be formulated for separate administration and are administered concurrently or sequentially.

For example, the anti-CTLA-4 antibody can be administered first followed by (e.g., immediately followed by) the administration of the anti-KIR antibody, or vice versa. Such concurrent or sequential administration preferably results in both antibodies being simultaneously present in treated patients.

In one embodiment, the anti-KIR and anti-CTLA-4 antibodies are administered on (1) day 1, week 1, (2) day 22, week 4, (3) day 43, week 7, and (4) day 64, week 10 of the induction phase. In another embodiment, the induction phase ends on day 84 of week 12. In another embodiment, the anti-KIR and anti-CTLA-4 antibodies are administered on day 1 of week 24, day 1 of week 36, day 1 of week 48, and day 1 of week 60 of the maintenance phase.

VI. Treatment Protocols

Suitable treatment protocols for treating a human patient afflicted with cancer include, for example, those comprising administering to the patient an effective amount of each of:

(a) an anti-KIR antibody comprising CDR1, CDR2 and CDR3 domains in a heavy chain variable region having the sequences set forth in SEQ ID NO:3, and CDR1, CDR2 and CDR3 domains in a light chain variable region having the sequences set forth in SEQ ID NO:5 and (b) an anti-CTLA-4 antibody comprising CDR1, CDR2 and CDR3 domains in a heavy chain variable region having the sequences set forth in SEQ ID NO:19, and CDR1, CDR2 and CDR3 domains in a light chain variable region having the sequences set forth in SEQ ID NO:20, wherein the anti-KIR antibody and anti-CTLA-4 antibody are first administered in combination (A) every 3 weeks for a total of 4 doses over 12 weeks during an induction phase, followed by (B) every 12 weeks for 4 doses starting at week 24 during a maintenance phase, and wherein the anti-KIR antibody is administered at a dose of 0.1-20 mg/kg, and the anti-CTLA-4 antibody is administered at a dose of 0.1-20 mg/kg during both phases.

In certain embodiments, each dose of the anti-KIR antibody is administered at 0.1, 0.3, 1, 3, 5 or 10 mg/kg. In preferred embodiments, each dose of the anti-KIR antibody is administered at 0.3, 1 or 3 mg/kg.

In other embodiments, each dose of the anti-CTLA-4 antibody is administered at 0.1, 0.3, 1, 3, 5 or 10 mg/kg body weight. In preferred embodiments, each dose of the anti-CTLA-4 antibody is administered at 1, 3 or 10 mg/kg. In more preferred embodiments, the anti-CTLA-4 antibody is administered at a dose of 3 mg/kg.

In one embodiment, the anti-KIR antibody and anti-CTLA-4 antibody are administered at the following doses during either phase:

(a) 0.1 mg/kg anti-KIR antibody and 3 mg/kg of anti-CTLA-4 antibody;

(b) 0.3 mg/kg anti-KIR antibody and 3 mg/kg of anti-CTLA-4 antibody;

(c) 1 mg/kg anti-KIR antibody and 3 mg/kg of anti-CTLA-4 antibody;

(d) 3 mg/kg anti-KIR antibody and 3 mg/kg of anti-CTLA-4 antibody;

(e) 3 mg/kg anti-KIR antibody and 10 mg/kg of anti-CTLA-4 antibody; or (f) 10 mg/kg anti-KIR antibody and 10 mg/kg of anti-CTLA-4 antibody.

In one embodiment, the anti-KIR and/or anti-CTLA-4 antibody is dosed in amount and at a frequency that results in substantially complete saturation of the NK cell inhibitory receptor (NKCIR) on NK cells for a period of at least about 1 week, at least about 2 weeks, or at least about 1 month. Accordingly, in one embodiment, a therapeutically active amount of one or more of the antibodies is an amount of the antibody that results in substantially complete NKCIR saturation on NK cells for a period of at least about 1 week, about 2 weeks, or about 1 month, following administration of the antibody, where the antibody is administered several times at a dosing frequency of once about every 2 weeks, once about every month, or once about every 2 months or longer, and the subsequent doses are separated by about 2 weeks or about 1 month.

In another embodiment, the anti-KIR and/or anti-CTLA-4 antibody is administered in a dosage range of about 0.1 mg/kg to about 3.0 mg/kg, about 0.3 mg/kg to about 3.0 mg/kg, about 0.1 mg/kg to about 1.0 mg/kg, or about 1.0 mg/kg to about 3.0 mg/kg. Preferably, the antibody is administered about once every 2 months.

In another aspect, any one of the various above-described methods may further optionally be modified by application of a chemotherapy treatment with one or more additional anti-cancer agents, e.g., chemotherapy agents.

In another embodiment, compositions are provided that contain an antibody according to the invention and a pharmaceutically acceptable carrier or excipient, which upon administration to an average human subject (about 100-200 pounds in weight) result in a dosage range of about 0.1 mg/kg to about 3.0 mg/kg, about 0.3 mg/kg to about 3.0 mg/kg, about 0.1 mg/kg to about 1.0 mg/kg, or about 1.0 mg/kg to about 3.0 mg/kg. In a particular embodiment, the composition results in a dosage range of about 0.1-0.3 mg/kg, and more specifically 0.2 mg/kg or about 0.3 mg/kg upon administration to an average human subject.

In another embodiment, the dose of the anti-KIR and/or anti-CTLA-4 antibody is varied over time. For example, the anti-KIR antibody and/or anti-CTLA-4 antibody may be initially administered at a high dose and may be lowered over time. In another embodiment, the anti-KIR antibody and/or anti-CTLA-4 antibody is initially administered at a low dose and increased over time.

In another embodiment, the amount of the anti-KIR and/or anti-CTLA-4 antibodies administered is constant for each dose. In another embodiment, the amount of antibody administered varies with each dose. For example, the maintenance (or follow-on) dose of the antibody can be higher or the same as the loading dose which is first administered during the induction phase. In another embodiment, the dose of the antibody administered during the maintenance phase can be lower or the same as the loading dose administered during the induction phase.

The antibodies described herein can be administered to a subject by any suitable means. In one embodiment, the anti-KIR and anti-CTLA-4 antibodies are formulated for intravenous administration.

In one embodiment, the anti-KIR and anti-CTLA-4 antibodies are administered on (1) day 1, week 1, (2) day 22, week 4, (3) day 43, week 7, and (4) day 64, week 10 of the induction phase. In another embodiment, the induction phase ends on day 84 of week 12. In another embodiment, the anti-KIR and anti-CTLA-4 antibodies are administered on day 1 of week 24, day 1 of week 36, day 1 of week 48, and day 1 of week 60 of the maintenance phase.

In other embodiments, the anti-KIR and/or anti-CTLA-4 antibodies are administered once per week, once every or three two weeks, once per month for as long as clinical benefit is observed or until unmanageable toxicity or disease progression occurs.

In another embodiment, a cycle of administration is eight weeks, which can be repeated, as necessary. In another embodiment, the treatment consists of up to 12 cycles.

In another embodiment, 4 doses of the anti-PD-1 antibody are administered per eight week cycle. In another embodiment, 2 doses of the anti-KIR antibody are administered per eight week cycle.

In another embodiment, the anti-CTLA-4 antibody and anti-KIR antibody are administered as a first line of treatment (e.g., the initial or first treatment). In another embodiment, the anti-PD-1 antibody and anti-KIR antibody are administered as a second line of treatment (e.g., after the initial or first treatment, including after relapse and/or where the first treatment has failed).

VII. Outcomes

With respect to target lesions, responses to therapy may include:

| | |
|---|---|
| Complete Response (CR) (RECIST V1.1) | Disappearance of all target lesions. Any pathological lymph nodes (whether target or non-target) must have reduction in short axis to <10 mm. |
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (i.e., Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (i.e., the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (i.e., the sum of the diameters at nadir of target lesions and any new measurable lesions increases by the required amount) Non-target lesions are not considered in the definition of Stable Disease and Partial Response. |

In exemplary outcomes, patients treated according to the methods disclosed herein may experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In some embodiments, administration of effective amounts of the anti-KIR antibody and anti-CTLA-4 antibody according to any of the methods provided herein produce at least one therapeutic effect selected from the group consisting of reduction in size of a tumor, reduction in number of metastatic lesions appearing over time, complete remission, partial remission, stable disease, or a complete response. In some embodiments, the provided methods of treatment produce a comparable clinical benefit rate (CBR=CR+PR+SD≥6 months) better than that achieved by an anti-KIR antibody or anti-CTLA-4 antibody alone. In other embodiments, the improvement of clinical benefit rate is about 20% 20%, 30%, 40%, 50%, 60%, 70%, 80% or more compared to an anti-KIR antibody or anti-CTLA-4 antibody alone.

VIII. Kits and Unit Dosage Forms

Also provided herein are kits which include a pharmaceutical composition containing an anti-KIR antibody, such as lirilumab, and an anti-CTLA-4 antibody, such as ipilimumab, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the anti-KIR or anti-CTLA-4 antibody for a single administration in accordance with the methods provided above. Instruments or devices necessary for administering the pharmaceutical composition(s) also may be included in the kits. For instance, a kit may provide one or more pre-filled syringes containing an amount of the anti-KIR or anti-CTLA-4 antibody.

In one embodiment, the present invention provides a kit for treating a cancer in a human patient, the kit comprising:

(a) a dose of an anti-KIR antibody comprising CDR1, CDR2 and CDR3 domains in a heavy chain variable region having the sequences set forth in SEQ ID NO:3, and CDR1, CDR2 and CDR3 domains in a light chain variable region having the sequences set forth in SEQ ID NO:5;

(b) a dose of an anti-CTLA-4 antibody comprising CDR1, CDR2 and CDR3 domains in a heavy chain variable region having the sequences set forth in SEQ ID NO:19, and CDR1, CDR2 and CDR3 domains in a light chain variable region having the sequences set forth in SEQ ID NO:20, (c) instructions for using the anti-KIR antibody and anti-CTLA-4 antibody in the method of any one of claims 1-16.

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Example 1

Phase I Clinical Trial with IPH-2101

IPH-2101 (also known as 1-7F9 and described in WO 2006/003179) is a fully human anti-KIR monoclonal antibody that binds specifically, and with high affinity, to KIR2DL-1, 2 and 3 and KIR2DS-1 and 2, thus preventing interaction between KIR and HLA-C. A Phase I clinical trial with IPH-2101 in patients with AML has been completed. Single administration at doses of 0.0003, 0.003, 0.015, 0.075, 0.3, 1 and 3 mg/kg did not reach a maximally tolerated dose. Two Phase I studies and three Phase II studies are ongoing in patients with AML or multiple myeloma (Vey N et al. (2012) Blood 120(22):4317-23; Benson D M et al. (2012) Blood 120(22):4324-33). In these studies, various dose levels were tested up to 3 mg/kg at an interval of every four weeks and the maximum number of cycles administered was six. Pharmacokinetic studies suggested a half life of 12-14 days at doses higher than 0.3 mg/kg. At a dose of 0.075 mg/kg, full KIR occupancy (>90%) was seen for less than 7 days. At a dose of 0.3 mg/kg, KIR occupancy decreased to less than 90% beginning on day 28. Sustained full KIR occupancy over four weeks was achieved at a dose of 3 mg/kg.

As of Dec. 1, 2011, clinical safety data was available for 136 patients in these trials. Adverse events (AE) were reported in 128 of 136 (94%) subjects and included 183 of 734 (25%) reports that were possibly, probably, or definitely related to IPH-2101. AEs that were reported in more than one subject included general symptoms (chills, pyrexia, fatigue, weakness), gastrointestinal symptoms (nausea, vomiting, diarrhea), neurological symptoms (dizziness, headache, tremors), pulmonary symptoms (dyspnea), skin symptoms (erythema, pruritus, rash), others (flushing, hypertension, muscle spasms, myalgia), and laboratory abnormalities (hyperkalemia, increased lipase, decreased counts in leukocytes, neutrophils and platelets). These events were mostly Grade 1 and Grade 2 and tended to be more frequent at doses greater than 1 mg/kg. Only one patient with multiple myeloma experienced a serious adverse event (SAE), which was due to acute renal failure. Although deemed related to IPH-2101, the patient also had disease progression. Overall, IPH-2101 was tolerable at doses from 0.0003 to 3 mg/kg.

Example 2

Pre-Clinical Pharmacology of Anti-KIR Antibody (Lirilumab)

Lirilumab is a fully human, IgG4 monoclonal antibody that binds specifically and with high affinity to a subset of KIRs, namely KIR2DL-1, 2 and 3 and KIR2DS-1 and 2. Surface plasmon resonance analysis demonstrated that the mean monovalent affinity of lirilumab for recombinant soluble KIR2DL1 was $2.04 \times 10^{-8}$ M (s.d. $0.31 \times 10^{-8}$) and that for KIR2DL3 was $3.01 \times 10^{-10}$ M (s.d. $0.41 \times 10^{-10}$) (data not shown).

Example 3

Lack of Toxicity of Anti-KIR Antibody (Lirilumab) in Mice

Neither lirilumab nor IPH-2101 binds to NK cells from non-human primate or other species traditionally used for safety testing. However, Ly49C/I are murine inhibitory receptors that are functionally homologous to human KIR. There were no adverse findings in mice treated with lirilumab at 10 mg/kg once weekly for four weeks, or with the surrogate anti-Ly49 antibody 5E6 F(ab')2 twice weekly for 13 weeks (data not shown).

Example 4

Clinical Pharmacology and Safety of Anti-KIR Antibody (Lirilumab)

Safety data for the 136 subjects treated with IPH-2101 is described above in Example 1. Lirilumab comprises the same heavy and light chain variable regions as IPH-2101 (also known as 1-7F9), and thus binds to the same epitope as IPH-2101, but differs from IPH-2101 in that (1) it is prepared in Chinese hamster ovary (CHO) cells, whereas IPH-2101 is prepared from hybridoma cells, and (2) a stabilizing hinge mutation (S231P) has been introduced into lirilumab.

Preliminary pharmacodynamic assessment of KIR occupancy revealed that all three subjects who received 0.015 mg/kg of lirilumab had full saturation of KIR2D (>90% KIR occupancy) for less than 1 week. Subjects who received 0.3 mg/kg had full saturation for at least 8 weeks, which was prolonged even longer in those who received higher doses. Half of subjects (0.015, 0.3, 1 and 3 mg/kg), including all three in the last cohort tested, had modest transient increases in levels of interferon gamma (data not shown).

Additionally, a Phase I study involving a related antibody, IPH2101 (also designated 1-7F9 in WO 2006/003179), having identical variable regions to lirilumab, but lacking a stabilizing S241P hinge mutation) has been completed for subjects with advanced hematological and solid malignancies (Vey N et al. (2012) Blood 120(22):4317-23; Benson D M et al. (2012) Blood 120(22):4324-33). As of May 7, 2012, twenty subjects received lirilumab at dose levels of 0.015, 0.3, 1, 3, 6, and 10 mg/kg. Six subjects had solid tumors (4 ovarian, 1 endometrial, 1 breast cancer) and 14 had hematological malignancies. The subjects in the lower three dose levels received four doses given at an interval of every four weeks. The subjects at the higher dose levels of 3, 6, and 10 mg/kg received one dose. There were no dose limiting toxicities. There was no trend in the frequency of AEs in relation to dose level. Eighteen of 20 (90%) subjects reported AEs. Most events were grade 1 (65%) or grade 2 (23%) in severity. Of a total of 111 AEs, 38 (34%) were considered related to lirilumab, the most common of which were fatigue (16%), headache (13%), pruritus (11%), asthenia (5%), constipation (5%), hypertension (5%), peripheral edema (5%) and rash (5%). There was only one grade 3 event that was related to lirilumab that occurred in a subject who received one dose at 6 mg/kg. This was an increase in lipase in a subject who entered the study with a grade 2 increase in lipase that returned to baseline 22 days later. There were no SAEs.

Example 5

Pharmacokinetics of Anti-KIR Antibody (Lirilumab)

Pharmacokinetic results from the on-going phase I study are pending. However, a PK model suggests that the PK profile of lirilumab is likely to be comparable to IPH-2101. In previous IPH-2101 phase I clinical trials in subjects with AML and multiple myeloma, a 2-compartment model with first order elimination was found to adequately describe the data with dose-dependent clearance, such that clearance decreased with increasing doses. The terminal half-life at the highest dose (3 mg/kg) was determined to be 18 days, which is consistent with reported values in the literature.

Example 6

Pre-Clinical Pharmacology of Anti-CTLA Antibody (Ipilimumab)

Ipilimumab has specificity and a high affinity for human CTLA-4. The calculated dissociation constant (KD) value from an average of several studies was 5.25 nM. Binding of ipilimumab to purified, recombinant human CTLA-4 antigen was also demonstrated by enzyme-linked immunosorbent assay (ELISA), with half-maximal binding at 15 ng/mL, whereas saturation was observed at 0.1 ug/mL. No cross-reactivity was observed against human CD28. Ipilimumab completely blocked binding of CD80 and CD86 to human CTLA-4 at concentrations higher than 6 ug/mL and 1 ug/mL, respectively (data not shown).

Example 7

Pharmacokinetics of Anti-CTLA Antibody (Ipilimumab)

The population PK (PPK) of ipilimumab was developed with 420 subjects (1767 serum concentrations) with advanced melanoma in phase 2 studies (CA184007, CA184008, and CA184022). Subsequently, the final PPK model was evaluated by an external model validation dataset from CA184004 (79 subjects with 328 serum concentration data). The PPK analysis demonstrated that PK of ipilimumab is linear and exposures are dose proportional across the tested dose range of 0.3 to 10 mg/kg, and the model parameters are time-invariant. The ipilimumab clearance (CL) of 15.3 mL/h from PPK analysis is consistent with that determined by PK analysis. The terminal half-life and apparent volume of distribution at steady state (Vss) of ipilimumab calculated from the model were 14.7 days, and 7.21 L, which are consistent with that determined by non-compartmental analysis. Volume of central and peripheral compartment were found to be 4.16 and 3.22 L, respectively, suggesting that ipilimumab first distributes into plasma volume and subsequently into extracellular fluid space. CL of ipilimumab was found to increase with increase in body weight, supporting dosing of ipilimumab based on a weight normalized regimen. Other covariates had effects that were either not statistically significant or were of minimal clinical relevance (data not shown).

Example 8

Inhibition of Tumor Growth in vivo by Combination Treatment with Anti-KIR Antibody and Anti-CTLA-4 Antibody An experiment was conducted in a murine acute myeloid leukemia (AML) model to test the hypothesis that the combination of anti-KIR and anti-CTLA-4 would potentiate anti-tumor efficacy. The rationale was to utilize pharmaceutical manipulation to coordinately regulate innate and adaptive immunity and recapitulate the biology seen in post-allogeneic transplant patients who have KIR mismatch. Both ipilimumab (anti-human CTLA-4 antibody) and lirilumab (anti-human KIR antibody) recognize only human sequences. Thus, a murine specific CTLA-4 antibody and an anti-Ly49 F(ab')$_2$ that recognizes Ly49C/I (which is the KIR homologue in mice; Parham P (2005) *Nature Reviews Immunology* 5:201-214) were used to test this hypothesis.

Mice were infused with the murine leukemia cell line, C1498, and randomized to one of four cohorts to receive control IgG antibody, anti-CTLA-4 monoclonal antibody, anti-Ly49 F(ab')$_2$, or both anti-CTLA-4 antibody and anti-Ly49 F(ab')$_2$. As shown in FIG. 1, mice treated with control IgG antibody had a median survival of 25.5 days. Mice treated with anti-CTLA-4 did not differ significantly from control animals (median survival of 26.0 days, p=0.37), whereas those treated with anti-Ly49 had prolonged survival (median survival of 27.0 days, p=0.016). Mice treated with both antibodies had further prolonged survival (median survival of 29.5 days, p<0.001). These results provide pre-clinical evidence of the ability of an anti-KIR antibody to synergistically (i.e., more than additively) potentiate the efficacy of an anti-CTLA-4 antibody in a murine liquid cancer (AML) model. This combination of antibodies has also been tested using a MC38 murine solid tumor (colon cancer) model (see Examples 9 and 10).

Example 9

Generation and Characterization of Transgenic Mouse MC-38 Colon Carcinoma Cell Line Model A pre-clinical mouse model for studying the effects of anti-KIR and anti-CTLA-4 antibodies was generated using a mouse colon carcinoma HLA-cw3-transduced MC-38 cell line subcutaneously engrafted in KIR2DL3 transgenic C57B1/6 mice (KIR-TgB6 mice).

Human KIR2DL3 transgenic CD158b×C57BL/6 mice (also referred to as KIR2DL3tg-B6 or KIRtg-B6 mice) have been described by Sola C et al. ((2009) *Proc Natl Acad Sci USA* 106: 12879-12884). The human NK inhibitory KIR2DL3 receptor is expressed on all NK and T lymphocytes in these mice. Mice were fed and housed under sterilized conditions.

Anti-CTLA-4 antibodies and their control isotypes mAbs were injected intra-peritoneally with a 1-ml syringe connected to a 30G1/2 needle. Anti-KIR antibody (clone GL183, which binds and inhibits human KIR2DL2/3) and its control isotype were injected intravenously (30G1/2 connected needle to 1-ml syringe). The injected volume of solutions was adjusted to the body weight of each animal, so as to inject 10 ml/kg, e.g., a 20-g mouse received 200 μl of solution. Administration of anti-NK1.1 (100 μg/100 μl/mouse, whatever its body weight) was performed intravenously into the caudal vein with a 1-ml syringe connected to a 30G1/2 needle.

Parental MC38 is a colon carcinoma cell line. MC-38 cw3, clone D31, was obtained after three transductions of the parental cell line with HLA-cw3. Cells were cultured in DMEM medium (GIBCO™) supplemented with 10% of decomplemented fetal bovine serum (FBS) and 1 mM Sodium Pyruvate (GIBCO™, 1136-039). After thawing, cells were seeded at 20,000 cells$cm^2$. For the subsequent passages, cells were detached with PBS supplemented with 2 mM of EDTA and seeded between 5,000 and 7,000 cells/$cm^2$ in T75 or T175 flasks, depending on the number of cells required. Cells were never cultured for more than 3 weeks.

Mice were subcutaneously engrafted with $5\times10^5$ tumor cells. 100 μl of the tumor cell suspension ($5\times10^6$ cells/ml) was injected in the right flank of KIR-tgB6 mice (whose hind flank was preliminary shaved) with a 1-ml syringe and 30G1/2 needle.

The following parameters were used to assess antitumoral activity.

Anti-Tumoral Parameters

Evaluation of the antitumoral activity of the different treatments performed was assessed by calculation of anti-tumoral parameters. Briefly, exponential growth fit was extrapolated from individual tumoral growth curves using GraphPad Prism software for the calculation of TGI, TGD and DT.

Tumor growth delay (TGD) is the delay of a treated group to reach a selected volume compared to the control: TGD=T−C, where T=median time (days) required for the treatment group tumors to reach a predetermined size and C=median time (days) required for the control group tumors to reach the same size.

Tumor growth inhibition (TGI) is the percentage of inhibition of growth compared to the control: TGI=(1−T/C)× 100, where T=median size (tumor volume) for the treatment group tumors reached at a predetermined day, and C=median size (tumor volume) for the treatment group tumors reached at the same day.

Doubling Time (Td or DT) is the time required for doubling the volume of the tumor.

When a treatment had a strong anti-tumoral activity, the exponential growth fit could not be extrapolated, precluding the calculation of anti-tumoral parameters. In this case, anti-tumoral activity was evaluated primarily based on the tumor growth curves profile.

Tumor Growth Curves Profile

For each group of mice, partial regression (PR), complete regression (CR) and temporary complete regression (TCR) was evaluated.

PR is defined by two consecutive reductions of the tumor volume from a selected volume. To be significant and different from the intra-individual measurement variations, each reduction has to be more than 17% from the previous measure.

CR is defined by a tumor volume that reaches 0 and is maintained to 0

TCR: is defined by a tumor volume that reaches 0 at least once and starts again to grow.

Survival Curves

Kaplan Meier survival curves were assessed on the day when tumor volumes reached 2000 $mm^3$. The survival medians were calculated with GraphPad Prism software.

Statistical Analysis

Survival curves were compared using the Log-rank (Mantel-Cox) test with GraphPad Prism software. Curves were considered significantly different and noted * when p<0.05, or ** when p<0.01.

A comparison of different groups at a determined day was performed as follows:
  Analysis of the Gaussian distribution by a normality test;
  If the normality test was passed, a one-way ANOVA analysis of variance was performed followed by a post-test;
  If the normality test is not passed, a Kruskal-Wallis non-parametric test was applied followed by a Dunn's multiple comparison.

Results for efficacy are abbreviated as follows:
  TF: Tumor Free (mice did not develop tumors after engraftment);
  PR: Partial Regression;
  CR: Complete Regression;
  TCR: Temporary Complete Regression;
  DT: Doubling time;
  MS: Survival Median.

Influence of HLA-cw3 Expression by MC-38 on Tumor Growth

Several experiments were performed in order to characterize the growth of MC38-cw3 tumors in the KIR-TgB6 mouse model and to determine the contribution of NK cells and, in particular, the interactions of NK cell surface-expressed KIR2DL3 with tumor cell surface-expressed HLA-cw3, in a setting where treatment is started after tumors are established (day 5).

In KIR-TgB6 mice, KIR2DL3 receptors have previously been described as functional, i.e., able to generate inhibitory signals of NK cell activation in experiments of splenocyte transfers by intravenous (iv) route (Sola et al., (2009) *Proc Natl Acad Sci USA* 106: 12879-12884). To analyze the contribution of the interactions between HLA-cw3 and KIR2DL3 receptors on the growth of subcutaneously engrafted MC38-cw3 tumors, the growth of MC38-eGFP cells was first compared to MC38-cw3 cells engrafted at the same dose in KIR-TgB6 mice. MC38-eGFP cells were used as a control for transduction and are not a formal mock counterpart of MC38-cw3 cells (as they were not transduced by an empty vector). After transduction, cells were cloned as described for MC38-cw3 cells. The clone D31 was selected for MC38-cw3 cells and the clone B25 was selected for MC38-eGFP cells.

The expression of several surface markers, in particular activating and inhibitory ligands for NK and T cells receptors, was compared on both selected clones, since a difference in expression of these markers could have an impact on tumor growth (independent of HLA-cw3 expression), and induce differences in recognition by NK or T cells. However, no major difference in expression of activating and inhibiting ligands was observed.

The growth of both clones subcutaneously engrafted at a dose of $5 \times 10^5$ cells in KIR-TgB6 mice was compared. The experimental setting is summarized in Table 1.

TABLE 1

Experimental Setting for Comparing Growth of MC-38GFP and MC-38-cw3 Tumor Cells in TgB6 Mice

| Groups | Treatment (D = day) | | n = | Mean Volume at randomization | Day of randomization |
|---|---|---|---|---|---|
| MC38-eGFP | Untreated | Untreated | 10 | unpalpable | |
| MC38-cw3 | PBS 10 ml/kg | D5, 12, 20, 26, 33 | 13 | unpalpable | 5 |

There was no CR, PR or TCR among the mice. However, two of the ten mice engrafted with MC38-eGFP cells remained tumor free (TF). MC38-cw3 cells express both murine and human Major Histocompatibility Complex (MHC) Class I molecules. NK cells from KIR-TgB6 mice both express the human NK inhibitory receptor KIR2DL3 and murine NK inhibitory receptors with endogenous ligands (Ly49 C and I and NKG2A). MC38-cw3 cells express both murine ($H-2^b$) and human NK inhibitory ligands (HLA-cw3). Interactions of NK human and mouse inhibitory receptors with their respective ligands on tumor MC38-cw3 cells generate NK inhibitory signals. This inhibits NK cell cytolytic activity, which allows tumor growth and explains why all tumors grow in KIR-TgB6 mice. On the contrary, MC38-eGFP only express murine MHC Class I molecules. Consequently, MC38-eGFP cells induce fewer inhibitory signals to NK cells, which could explain why 20% of the MC38-eGFP-engrafted KIR-TgB6 mice remained tumor free.

NK Influence on MC38-cw3 Tumor Growth in KIR-TgB6 Mice

MC38 tumor growth in B6 mice was previously described to be T cell-dependent. It was, therefore, necessary to evaluate the role of NK cells on the growth of MC38-cw3 cells in KIR-TgB6 mice. To evaluate this point, an experiment was conducted in which $5 \times 10^5$ MC38-cw3 cells were subcutaneously engrafted on the right flank of KIR-TgB6 mice. One group of mice (n=10) was NK depleted by intravenous injection of 100 µg of anti-NK1.1 mAb on days 0, 14, 28, while the control group (n=10) received 10 ml/kg of the vehicle (PBS) at the same time. Tumor dimensions were measured twice a week with a digital caliper and the tumor volume (V) calculated according to the following formula:

$$V = (A \times B^2)/2 \text{ with } A = \text{length and } B = \text{width.}$$

Results are shown in Table 2.

TABLE 2

Role of NK Cell Depletion on Growth of MC38-cw3 Cells in TgB6 Mice

| Group | TF | PR | CR | TCR | DT (median days) | MS (days) | End of Exp. (day) |
|---|---|---|---|---|---|---|---|
| PBS | 0/10 | 0/10 | 0/10 | 0/10 | 5.7 ± 3.4 | 35 | 39 |
| NK1.1 | 0/10 | 0/10 | 0/10 | 0/10 | 6 ± 1.3 | 32 | |

Overall, the impact of NK cells on tumor progression was minimal. In NK-depleted mice, MC38-cw3 tumors seemed to progress more quickly than MC38-eGFP ones, especially at early time points. This tendency was confirmed by values of survival medians, which were about 32 days for the NK-depleted group and 35 days for the control group. However, the doubling time values were quite similar. This demonstrates that NK cells could have an anti-tumor effect while the tumors are not fully established. This early involvement of NK cells could be enhanced by the expression of some activating ligands by tumor cells. However, when tumors grow and become established, the expression of these ligands could be decreased, thus reducing the level of NK cell activation. This may be true for CD155, one of the ligands of the NK activating receptor DNAM-1, which is strongly expressed in vitro by MC38-cw3 cells. A decrease of DNAM-1 expression was observed on the surface of established tumors. In addition, once tumors are established, tumor cells are reported to secrete soluble factors, thereby preventing the recruitment of NK cells on the site of tumor area.

Example 10

Inhibition of Tumor Growth in vivo by Combination Treatment with Anti-KIR Antibody and Anti-CTLA-4 Antibody in Monotherapy-Resistant Cancer Model The objective of this series of experiments was to study the effects of the combination of anti-KIR2DL (GL183) and anti-CTLA-4 monoclonal antibodies on the development of tumors that are resistant to monotherapy The effects of the combination of both molecules were compared to the effects of each monotherapy. This pre-clinical model was based on the growth of a mouse colon carcinoma HLA-cw3-transduced MC-38 cell line subcutaneously engrafted in KIR2DL3 transgenic C57Bl/6 mice (KIR-TgB6 mice) (see Example 9).

Determination of Anti-KIR Dose and Setting to Combine with Anti-CTLA-4 Monoclonal Antibodies Intravenous (iv) administration of 20 mg/kg of anti-KIR mAb induced KIR receptor occupancy above 90% for 14 days in the whole blood of KIRtgB6 mice. In order to ensure maintenance of receptor occupancy above 90% for the duration of the experiment, two administration schedules were tested as shown in Table 3. Specifically, one injection of 10 mg/kg GL183 (KIR receptor occupancy above 90% for 8 days) or 20 mg/kg GL183 (KIR receptor occupancy above 90% for 14 days) was intravenously administered once a week for 5 weeks.

volumes indicated in Table 4 (500, 1000, 1500 and 2000 $mm^3$). The anti-tumor effect of anti-KIR mAb only impacted the anti-tumor parameters, doubling time and survival medians, for the dose of 20 mg/kg. However, neither dose gave rise to any PR, CR or TCR, as shown in Table 5.

TABLE 4

Effect of Anti-KIR Antibody on MC38-cw3 Tumor Growth Delay (TGD)

| | TGD (days) | | | |
|---|---|---|---|---|
| Group | 500 $mm^3$ | 1000 $mm^3$ | 1500 $mm^3$ | 2000 $mm^3$ |
| PBS | | | | |
| GL183 10 mg/kg | 3.9 | 4.0 | 4.8 | 4.5 |
| GL183 20 mg/kg | 4.5 | 9.0 | 10.8 | 12.1 |

TABLE 5

Effect of Anti-KIR Antibody on Anti-Tumor Parameters of MC38-cw3 Tumor Growth

| Group | TF | PR | CR | TCR | DT (median days) | MS (days) | End of Exp. (day) |
|---|---|---|---|---|---|---|---|
| PBS | 0/13 | 0/13 | 0/13 | 0/13 | 6.9 ± 1.1 | 36 | 67 |
| GL183 10 mg/kg | 0/11 | 0/11 | 0/11 | 0/11 | 6.5 ± 2.9 | 39 | |
| GL183 20 mg/kg | 0/13 | 0/13 | 0/13 | 0/13 | 8.7 ± 5.4 | 48 | |

TABLE 3

Administration Schedules for Administration of Anti-KIR Antibody

| Groups | Treatment (D = day) | n = | Mean Volume at randomization | Day of randomization |
|---|---|---|---|---|
| MC38-cw3 | PBS 10 ml/kg D5, 12, 20, 26, 33 | 13 | unpalpable | 5 |
| MC38-cw3 | GL183 10 mg/kg iv D5, 12, 20, 26, 33 | 15 | unpalpable | |
| MC38-cw3 | GL183 20 mg/kg iv D5, 12, 20, 26, 33 | 15 | unpalpable | |

$5 \times 10^5$ cells MC38-cw3 cells were subcutaneously engrafted on the right flank of KIR-TgB6 mice. On days 5, 12, 20, 26, 33, one group of mice (n=13) was intravenously treated with 10 ml/kg of PBS, a second group (n=15) was intravenously treated with 10 mg/kg of anti-KIR mAb (GL183) and the third group (n=15) received 20 mg/kg intravenously. Tumor dimensions were measured twice a week with a digital caliper and the tumor volume (V) was calculated according to the following formula:

$$V = (A \times B^2)/2 \text{ with } A=\text{length of tumor and } B=\text{width of tumor.}$$

Effects of Anti-KIR mAb on the Subcutaneous Growth of MC38-cw3 Engrafted in KIR-TgB6 Mice For both doses of saturating anti-KIR mAb treatment, MC38-cw3 tumor growth was slowed. This was confirmed by values of Tumor Growth Delay (TGD), which were still higher for the group treated with 20 mg/kg of anti-KIR compared 10 mg/kg one. This was true for the four tumor Combination of Anti-KIR mAb and Anti-Mouse CTLA-4 mAb Anti-KIR mAb was administered at the dose of 20 mg/kg once a week every week on days 7, 13, and 22 after engraftment of cells, in combination with anti-CTLA-4 mAb administered at the dose of 10 mg/kg on days 7, 11, and 14 after engraftment of cells. It is possible that an anti-tumor effect of an anti-KIR mAb is T cell-dependent in addition to being NK cell-dependent. However, it is also possible that the study of the combination of anti-KIR and anti-CTLA-4 would not permit the observation of any impact of NK cells on the anti-tumor effect of anti-KIR mAb, due to masking by the contribution T cells (since the human NK inhibitory KIR2DL3 receptor is expressed on all NK and T lymphocytes in the KIR-TgB6 mice).

Anti-CTLA-4 and Anti-KIR mAb Combination: First Experimental Series

In a first series of experiments, the combination of anti-mouse CTLA-4 and anti-KIR mAb was tested as shown in Table 6.

TABLE 6

Schedule for Testing Effect of Anti-Mouse CTLA-4 and/or Anti-KIR Antibodies on Tumor Growth

|  | Groups | Treatment (D = day) | n = | Mean Volume at randomization | Day of randomization |
|---|---|---|---|---|---|
| MC38-cw3 | PBS 10 ml/kg ip + PBS 20 ml/kg iv | D7, 11, 14/ D7, 14, 22 | 14 | 25.5 ± 17.6 | 7 |
| MC38-cw3 | PBS 10 ml/kg ip + GL183 20 mg/kg iv | D7, 11, 14/ D7, 14, 22 | 14 | 25.7 ± 17.1 | |
| MC38-cw3 | CTLA-4 10 mg/kg ip + PBS 20 ml/kg iv | D7, 11, 14/ D7, 14, 22 | 14 | 25.6 ± 17.4 | |
| MC38-cw3 | CTLA-4 10 mg/kg ip + GL183 20 mg/kg iv | D7, 11, 14/ D7, 14, 22 | 14 | 25.6 ± 17.3 | |

The results (Table 7) show that in this experimental setting, neither anti-CTLA-4 mAb nor anti-KIR mAb had an anti-tumor effect when administered as monotherapy. One partial regression was observed in the group of mice treated with anti-KIR mAb. However, the combination of anti-CTLA-4 mAb and anti-KIR mAb gave rise to two complete and two partial regressions and an increase of median survivals, which shows the therapeutic benefits of the combinations of both molecules.

In this experimental setting, only the anti-KIR mAb, when used as monotherapy, allowed a slight slowing of tumor progression with one CR, but this tendency has no impact on tumor parameters. In contrast, the combination of both molecules produced a strong anti-tumor effect characterized by two PRs and an increase of doubling time and median survival values, as shown in Table 9.

TABLE 7

Effect of Anti-Mouse CTLA-4 and/or Anti-KIR Antibodies on Tumor Growth

| Group | TF | PR | CR | TCR | DT (median days) | MS (days) | End of Exp. (day) |
|---|---|---|---|---|---|---|---|
| PBS 10 ml/kg ip + PBS 20 ml/kg iv | 0/14 | 0/14 | 1/14 | 0/14 | 7 ± 1.4 | 37 | 48 |
| PBS 10 ml/kg ip + GL183 20 mg/kg iv | 0/12 | 0/12 | 0/12 | 0/12 | 7.1 ± 3.9 | 39 | |
| CTLA-4 10 mg/kg ip + PBS 20 ml/kg iv | 1/14 | 0/14 | 0/14 | 0/14 | 6.7 ± 0.9 | 39 | |
| CTLA-4 10 mg/kg ip + GL183 20 mg/kg iv | 0/13 | 2/13 | 2/13 | 0/13 | ND | 48 | |

Anti-CTLA-4 and Anti-KIR mAb Combination: Second Experimental Series

The first experimental series above was repeated on an additional set of mice according the schedule in Table 8.

TABLE 8

Revised Schedule for Testing Effect of Anti-Mouse CTLA-4 and/or Anti-KIR Antibodies on Tumor Growth

|  | Groups | Treatment (D = day) | n = | Mean Volume at randomization | Day of randomization |
|---|---|---|---|---|---|
| MC38-cw3 | isotype Ctrl GL183 (20 mg/kg) + isotype Ctrl CTLA-4 10 mg/kg ip | D8, 15, 22/ D8, 11, 15 | 15 | 18.3 ± 20 | 8 |
| MC38-cw3 | GL183 20 mg/kg + isotype Ctrl CTLA-4 10 mg/kg ip | D8, 15, 22/ D8, 11, 15 | 15 | 17.3 ± 18.3 | |
| MC38-cw3 | isotype Ctrl CL 183 20 mg/kg + CTLA-4 10 mg/kg ip | D8, 15, 22/ D8, 11, 15 | 15 | 15.9 ± 19.5 | |
| MC38-cw3 | GL183 20 mg/kg iv + CTLA-4 10 mg/kg ip | D8, 15, 22/ D8, 11, 15 | 15 | 17.3 ± 18.5 | |

TABLE 9

Effect of Anti-Mouse CTLA-4 and/or Anti-KIR Antibodies on Tumor Growth and Tumor Parameters

| Group | TF | PR | CR | TCR | DT (median days) | MS (days) | End of Exp. (day) |
|---|---|---|---|---|---|---|---|
| isotype ctrl GL183 20 mg/kg + isotype ctrl CTLA-4 10 mg/kg ip | 1/11 | 0/11 | 0/11 | 0/11 | 6.5 ± 1.8 | 45 | 100 |
| GL183 20 mg/kg + isotype ctrl CTLA-4 10 mg/kg ip | 1/11 | 0/11 | 1/11 | 0/11 | 6.7 ± 1.8 | 45 | |
| isotype ctrl GL183 20 mg/kg + CTLA-4 10 mg/kg ip | 1/11 | 0/11 | 0/11 | 0/11 | 5.8 ± 2.2 | 45 | |
| GL183 20 mg/kg iv + CTLA-4 10 mg/kg ip | 2/11 | 2/11 | 1/11 | 0/11 | 9 ± 2.4 | 60 | |

Example 11

Phase 1 Trial in Patients having Solid Tumors

A phase 1 trial of Anti-KIR Antibody (lirilumab) and Anti-CTLA-4 Antibody (ipilimumab) is conducted in patients having advanced solid tumors to demonstrate the efficacy of administering these two therapeutics as a combination treatment.

1. Objectives

The primary objective of this study is to assess the safety and tolerability, characterize the dose-limiting toxicities (DLTs), and identify the maximally tolerated dose (MTD) of lirilumab given in combination with ipilimumab in subjects with select advanced (metastatic and/or unresectable) solid tumors.

Secondary objectives include assessing the preliminary anti-tumor activity of the combination of lirilumab and ipilimumab in subjects with select advanced solid tumors, characterizing the pharmacokinetics (PK) of lirilumab, as well as to monitor sparse (peak and trough) concentrations of ipilimumab, when they are administered as a combination regimen, monitoring immunogenicity of lirilumab and ipilimumab when administered as a combination regimen, and assessing the pharmacodynamic effect in tumor tissue on tumor infiltrating lymphocyte (TIL) subsets from melanoma subjects treated with lirilumab given in combination with ipilimumab during cohort expansion.

Additional objectives include: assessing the pharmacodynamic effects of lirilumab versus dose and/or exposure given in combination with ipilimumab on select biomarkers in the peripheral blood during dose escalation, assessing the pharmacodynamic activity in tumor tissue and peripheral blood in subjects treated with lirilumab given in combination with ipilimumab in subjects with non-small cell lung cancer and castrate resistant prostate cancer, exploring potential associations between biomarker measures and antitumor activity and safety (adverse events), further characterizing KIR occupancy and NK function at multiple dose levels of lirilumab when given in combination with ipilimumab, assessing the potential association of KIR and HLA genotypes with anti tumor activity measures, and assessing the landmark overall survival at three years following the start of therapy with the combination of lirilumab and ipilimumab.

2. Study Design and Duration

This is a phase I, open label study with two segments: dose escalation and cohort expansion. Dose escalation is performed to characterize the safety and tolerability of lirilumab administered in combination with ipilimumab in subjects with select advanced solid tumors and is followed by the cohort expansion segment. Study treatment in both segments is divided into Induction and Maintenance, consistent with the general principles of ipilimumab therapy. Lirilumab and ipilimumab are administered concurrently through both Induction and maintenance. Subjects in the cohort expansion segment are treated at the maximally tolerated dose (MTD), the maximally administered dose (MAD), or at an alternative dose as determined by the investigators and the sponsor.

Subjects complete up to four periods of the study: Screening (up to 28 days), Treatment (Induction and Maintenance, up to a maximum of 1.4 years of study therapy), Clinical Follow-up (90 days), and Survival Follow-up (up to 3 years following the first dose of study drug). Subjects receive lirilumab in combination with ipilimumab in two distinct parts: Induction and Maintenance. During Induction, subjects receive intravenous (IV) doses of lirilumab in combination with ipilimumab every 3 weeks for a total of 4 doses. During Maintenance, subjects receive lirilumab in combination with ipilimumab therapy every 12 weeks for an additional 4 doses starting at week 24. The decision to treat a subject with additional cycles of study therapy is based on tumor assessment. Treatment decisions related to subject management are based exclusively on immune related (ir) response criteria, irRECIST (see Section 1.1.5 for the rationale and Appendix 4 for definitions). Subjects with an overall response of irCR, irPR, irSD, or irPD-unconfirmed continue therapy until they develop irPD-confirmed, experience clinical deterioration, develop adverse events requiring discontinuation, withdraw consent, or complete both Induction and Maintenance.

Subjects who: (1) complete Induction and Maintenance or (2) develop toxicity requiring discontinuation of the study therapies enter the Clinical Follow-up period until they have irPD-confirmed, initiate new treatment, or complete all Clinical Follow-up (Follow-up Visits 1 and 2; every 6 weeks for a total of 12 weeks). Subjects who have irPD-confirmed on study therapy enter Clinical Follow-up to continue monitoring for adverse events. At each Clinical Follow-up visit, assessments include physical examinations, adverse event assessment, safety laboratory testing and imaging. If an adverse event has not resolved by the end of the Clinical Follow-up period, the subject may continue follow-up until the AE has resolved to grade ≤1 or baseline, or deemed irreversible by the investigator.

Figure 2:
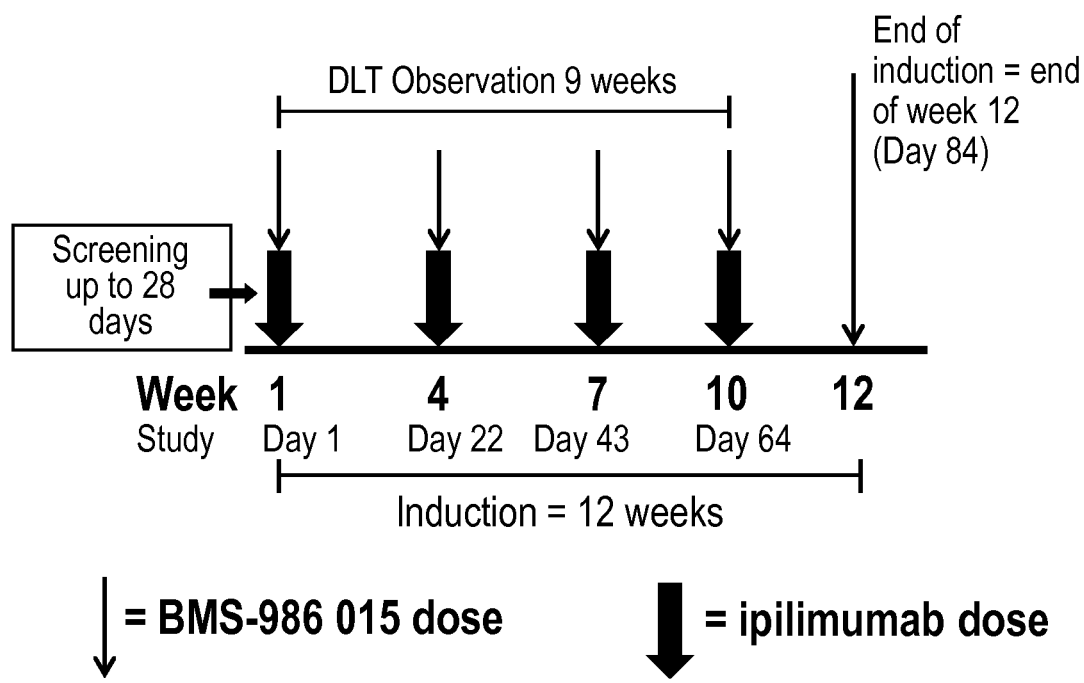
FIG. 2 is a schematic illustrating dosing during the induction phase for dose escalation and cohort expansion.
Figure 3:
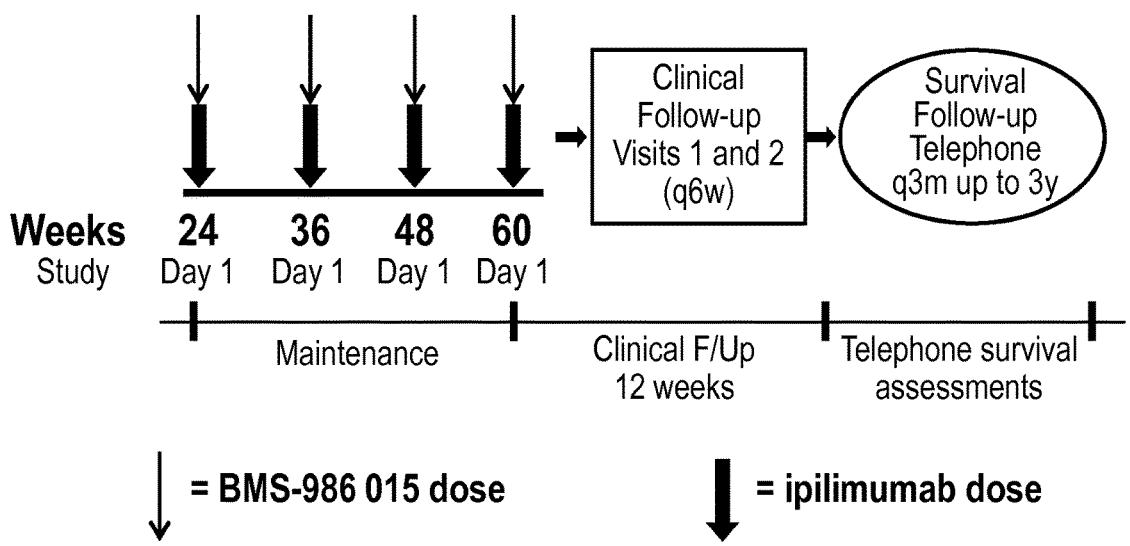
FIG. 3 is a schematic illustrating dosing during the maintenance phase for dose escalation and cohort expansion.

After completion of the Clinical Follow-up period, subjects then enter the Survival Follow-up period. During this period, clinic visits or telephone contact every 3 months are performed to assess survival status. The duration of this period is up to 3 years following the first dose of study drug. Subjects in survival follow-up who have progression of disease are eligible to receive anti-cancer therapy as appropriate. Study design schematics are presented below in FIGS. 2 (Induction) and 3 (Maintenance).

3. Dose Escalation

Six to nine subjects with advanced melanoma (MEL), advanced non-small cell lung cancer (NSCLC), and/or advanced castrate resistant prostate (CRPC) cancer patients are enrolled in successive cohorts assessing escalating doses of lirilumab administered in combination with ipilimumab. A 6+3 design is used to assess safety of ipilimumab given in combination with lirilumab. The dose selection table is provided in Table 10. The Dose Limiting Toxicity (DLT) observation period lasts 9 weeks from initiation of study therapy. Six (6) subjects are initially treated at a given dose level with expansion up to 9 subjects if two dose limiting toxicities are observed in the first 6 subjects. If 0 or 1 DLTs occur in a cohort of 6 subjects, dose escalation proceeds and subjects are enrolled at the next higher dose level. If 2 of 6 subjects in a cohort experience a DLT, 3 more subjects are enrolled at the same dose level in order to increase the confidence around the safety of that dose level. If 3 or more of 6 or 3 or more of 9 subjects experience DLTs within a cohort, then that dose level is determined to have exceeded the maximum tolerated dose (MTD). Exploration of intermediate dose ranges is added to expand the safety data at various dose levels of lirilumab given in combination with ipilimumab. If an MTD is not identified through cohort 5, then an additional cohort of patients to be treated with lirilumab at a dose of 10 mg/kg given in combination with 10 mg/kg ipilimumab is considered based on the aggregate safety experience during dose escalation.

To further explore emerging safety signals at any selected dose cohorts, a total of up to 12 subjects are accrued to any dose cohort during dose escalation. The additional enrollment is only permitted once the dose level in the cohort has been evaluated and declared safe for dose escalation. Only DLTs in the initial 6-9 subjects enrolled in a cohort are formally evaluated in the dose escalation and subsequent determination of the MTD. However, safety data from all treated subjects is considered in dose selection for cohort expansion.

No intra-subject dose escalation or reduction is allowed. Subjects who withdraw from the study during the DLT period for reasons other than toxicity are replaced within the same dose cohort. Subjects in dose escalation are continually monitored beyond the DLT period as well, to evaluate safety beyond the DLT period. All available clinical and laboratory data, and the nature, time of onset, and time to resolution of DLTs observed during dose escalation are reviewed to determine whether an alternate dose schedule should be examined in consultation between the investigators and the sponsor if needed. If agreed upon, the alternate schedule is identified by a protocol amendment. If the MTD is exceeded in the first cohort, the evaluation of alternate doses and schedules of lirilumab is investigated.

TABLE 10

Schedule of Planned Dose Escalation

| Dose Level | Lirilumab (IV; mg/kg) | Ipilimumab (IV; mg/kg) |
| --- | --- | --- |
| 1 | 0.1 | 3 |
| 2 | 0.3 | 3 |
| 3 | 1 | 3 |
| 4 | 3 | 3 |
| 5 | 3 | 10 |

4. Cohort Expansion

Cohort expansion is initiated at the MTD, the maximum administered dose (MAD), or an alternate dose, if recommended by the investigators and the sponsor. Approximately 20 subjects are treated in each of 3 cohorts (total 60 subjects). Each cohort limits enrollment to one of three specified tumor types; non-small cell lung cancer, melanoma, or castrate resistant prostate cancer, to establish expanded safety experience with the combination and to enable characterization of the immunoregulatory (biomarker) activity and preliminary anti-tumor efficacy of the lirilumab and ipilimumab combination.

Clinical safety monitoring of subjects enrolled during this additional cohort expansion portion of the study is identical to that conducted during the dose escalation portion of the study. If the combined incidence of study drug related DLTs exceeds 33% of treated subjects, further enrollment to that cohort is interrupted and the findings are discussed between the study investigators and the sponsor. An agreement is reached as to whether a lower dose or an alternate dose or dose schedule of the combination should be examined, or whether any additional treatment guidelines should be implemented prior to enrollment of additional subjects on study 5. Treatments The study treatments include lirilumab and ipilimumab. Lirilumab and ipilimumab are packaged in an open label fashion. Ipilimumab is administered as an IV infusion, followed by lirilumab administered as an IV infusion, on treatment weeks 1, 4, 7, 10, 24, 36, 48 and 60.

6. Dose Limiting Toxicities

Lirilumab has the potential to be synergistic with ipilimumab and augment the rate and duration of clinical responses. However, it also has the potential to augment the frequency and severity of previously characterized ipilimumab related events of special interest, as well as generate new drug related toxicities. To maximize the safety monitoring of the study drugs, the following measures described below are utilized.

Dose limiting toxicity (DLT) is determined based on the incidence, intensity and duration of AEs that are related to study drug, and that occur within 63 days (9 weeks) of initiation of study drug. The severity of AEs is graded according to the NCI CTCAEv4. For the purposes of subject management, a DLT leads to dose modification regardless of the cycle in which the DLT occurs.

Administration of both study drugs is discontinued if at least 1 of the following drug related AEs listed below occurs, regardless of whether it is during or after the DLT period. All adverse events that meet discontinuation criteria are reported within 24 hours.

Any of the following events is considered a Hepatic DLT:
ALT or AST>8×ULN, regardless of duration
ALT or AST>5× and <8×ULN, that fails to return to Grade 1 or less within 5 days despite medical intervention Grade 3 total bilirubin ALT or AST>3×ULN and concurrent total bilirubin >2× ULN Any of the following events are considered a Non-Hematologic DLT:

Grade 2 eye pain or reduction in visual acuity that requires systemic treatment

Grade 2 eye pain or reduction in visual acuity that does not respond to topical therapy and that does not improve to Grade 1 within 2 weeks of initiation of topical therapy Grade 3 Non-Hepatic or Non-Hematologic toxicity, with the following exceptions:

The Following Grade 3 Non-Hematologic events are not considered DLTs:

Grade 3 electrolyte abnormality that lasts less than 72 hours, is not clinically complicated, and resolves spontaneously or responds to conventional medical intervention Grade 3 increase in amylase or lipase that is not associated with clinical or radiographic evidence of pancreatitis Grade 3 nausea or vomiting that lasts less than 48 hours, and resolves to Grade 1 or less either spontaneously or with conventional medical intervention Grade 3 fever that lasts less than 72 hours, and is not associated with hemodynamic compromise (including hypotension, or clinical or laboratory evidence of end organ perfusion impairment)

Grade 3 endocrinopathy that is well controlled by hormone replacement

Grade 3 tumor flare (defined as pain, irritation or rash that localizes to sites of known or suspected tumor)

Grade 3 fatigue

Grade 3 infusion reaction that returns to Grade 1 in less than 6 hours

Any of the following events are considered a Hematologic DLT:

Grade 4 neutropenia that lasts longer than 5 days

Grade 4 thrombocytopenia

Grade 3 thrombocytopenia associated with clinically significant bleeding

Grade 3 febrile neutropenia that lasts longer than 48 hours

Grade 3 hemolysis

7. Guidelines for Dose Modification

No dose reductions of either lirilumab or ipilimumab are permitted in this study.

Patients who experience a DLT must have therapy held, pending resolution of the toxicity. If the adverse event resolves to grade 1 or less, or to baseline, in severity within 21 days, then therapy may resume at the same doses for both study drugs. If the toxicity resolves after 21 days, and the investigator believes that the subject is deriving clinical benefit, then the subject may be eligible to resume the study drugs, following the approval of the BMS medical monitor. If the subject then experiences a subsequent DLT, that also resolves and the investigator continues to believe that the subject is deriving clinical benefit, then the subject may be eligible to resume the study drugs.

A constellation of adverse events have been observed in patients treated with ipilimumab monotherapy. These events can include, but are not limited to: enterocolitis, dermatitis, hepatitis, endocrinopathies, and neuropathies. Based on broad clinical experience with ipilimumab, a unique set of criteria have been developed to define and manage dose-limiting toxicities in the context of these events. For AEs of interest felt to be related to ipilimumab, refer to the most current version of the ipilimumab Investigator Brochure (TB) for details on algorithms for recommended management of AEs.

Subjects are required to permanently discontinue both study drugs for the following:

Any grade 4 adverse event, with the exception of: grade 4 electrolyte abnormalities that resolves ≤72 hours, grade 4 neutropenia ≤5 days in duration, or grade 4 lymphopenia ≤5 days in duration.

Any adverse event with clinical risk is assessed on a case by case basis to determine the risks and benefits of continuing on therapy following resolution versus discontinuing therapy permanently. High grade events involving the central nervous system, eyes, liver or lung, normally require permanent discontinuation, unless there are elements of the individual's history and clinical course that suggests a higher likelihood of benefit over risk with continued therapy upon resolution.

8. Safety Assessments

Subjects are considered evaluable for safety if they have received any dose of either study drug. Toxicity assessments are continuous during the treatment phase and follow-up phases.

Adverse events are assessed continuously during the study and for 90 days after the last treatment. Adverse events are coded using the most current version of MedDRA and reviewed for potential significance and importance. Adverse events are evaluated according to the NCI CTCAE Version 4.0. Subjects are followed until all treatment related adverse events have recovered to baseline or are deemed irreversible by the investigator.

Laboratory tests may be repeated if clinically significant. Results of all laboratory tests required by this protocol must be provided, either recorded on the laboratory pages of the CRF or by another mechanism. If the units of a test result differ from those printed on the CRF, the recorded laboratory values must specify the correct units. Any abnormal laboratory test result considered clinically significant by the investigator must be recorded on the appropriate AE page of the CRF.

9. Efficacy Assessments

Disease assessment with computed tomography (CT) and/or magnetic resonance imaging (MRI), as appropriate, is performed at baseline and then at weeks 7, 13, 18, 24, 36, 48 and 60 until confirmed disease progression, at the completion of follow-up, or until subjects withdraw from the study. Disease assessment at other times points may be performed if the investigator is concerned about tumor progression. Tumor responses are determined as defined by RECIST v1.1 (Eisenhauer E A, *Eur J Cancer* 2009; 45:228-247), as well as by immune-related response criteria, irRECIST (Wolchok J D, et al., *Clin Cancer Res* 2009; 15:7412-7420)). Treatment decisions related to subject management are based exclusively on irRECIST criteria. Scans and measurements may be collected centrally to be reviewed by independent radiologists at a later date, or at any time during the study.

Changes in tumor measurements and tumor responses are assessed by the investigator using irRECIST criteria. Investigators also report the number and size of new lesions that appear while on-study. The timepoint tumor assessments are reported on the CRF based on investigators' assessment using irRECIST criteria. In addition, RECIST v1.1 time point assessments are derived programmatically.

10. Pharmacokinetic Assessments

The ipilimumab pharmacokinetic concentrations are measured to derive the trough (Cmin) and end of infusion concentration at specified visits. Pharmacokinetic of lirilumab is derived from serum concentration versus time data at specified time points. The pharmacokinetic parameters to be assessed include:

Cmax Maximum observed serum concentration
Cmin Minimum observed serum concentration
Tmax Time of maximum observed serum concentration
AUC(INF) Area under the serum concentration-time curve from time zero extrapolated to infinite time
AUC(TAU) Area under the concentration-time curve in one dosing interval
T-HALF Terminal plasma half-life
CL Clearance
Vss Volume of distribution at steady state
AI Accumulation Index Individual subject pharmacokinetic parameter values are derived by non compartmental methods by a validated pharmacokinetic analysis program. Actual times are used for the analyses.

Serial serum samples for lirilumab PK assessments and serum samples for assessment of ipilimumab peaks and troughs are collected. Lirilumab and ipilimumab samples in serum are analyzed for pharmacokinetics by a validated immunoassay. Additionally, lirilumab and ipilimumab samples are banked for potential exploratory pharmacokinetic analysis by an orthogonal bioanalytical method (eg, LC/MS-MS).

11. Biomarker Assessments

The sample collection and biomarker assessment strategy is designed to address key questions regarding the actions of lirilumab in combination with ipilimumab. Specifically, the measurements obtained from the various biomarker assessments help in understanding the immune modulation (pharmacodynamic effects) resulting from tandem activation of innate and adaptive immunity. Additionally, the relationship of KIR/HLA status is also examined as a potential indicator of clinical activity.

Tumor Biopsy:

Subjects in the melanoma expansion cohort must have at least one lesion large enough to undergo repeated biopsies (pre-treatment and on-treatment) or have at least two distinct lesions eligible for core needle or excisional biopsies until paired samples from at least 10 subjects of pre-treatment and on-treatment biopsies, are collected in the study. Subjects in the NSCLC and CRPC cohorts are encouraged to provide optional biopsies if of acceptable clinical risk. These lesions must not be target lesions or sites that have received prior radiation therapy. The biopsy is via core needle (minimum size 16 gauge, length>5 mm). At least one core biopsy is taken at each time point. However, collection of more tumor tissue is strongly encouraged, if deemed clinically safe by the investigator. Punch and excisional biopsies are also acceptable. The ideal minimal tumor volume is 150 mm$^3$. Pathologic confirmation is strongly encouraged at the time of tumor biopsy to confirm adequate tissue collection and biopsy quality. Detailed instructions of the obtaining, processing, labeling, handling, storage and shipment of these specimens is provided in a separate Procedure Manual at the time of study initiation. Subjects whose screening biopsy yields inadequate tissue quantity or quality are allowed to continue in the study, but no other biomarker samples are collected. That subject is replaced in order to obtain 10 subjects with paired pre-treatment and on-treatment biopsies. If subjects have a response to treatment, on-treatment biopsies may not be possible. In this case, subjects may also continue with the study and participate in other biomarker collections.

Tumor Biopsy Assessments:

Tumor biopsies are used to assess the identity and percentage of tumor infiltrating lymphocytes (TILs) present at screening and at week 13. Specific antibodies are used to distinguish the various TILs (NK cells, Treg cells, CTLs) present in tumor biopsy tissue by immunohistochemistry (IHC). In addition, tumor markers (i.e., PD-L1 and HLA class I) are also be evaluated by IHC. Additionally, sections from tumor biopsies collected pre-treatment and on-treatment are cryopreserved for potential future gene expression analyses. Genes of interest include, but are not limited to, PD-1, PD-L1, KIR and LAG-3. Simultaneous collection of peripheral blood/serum samples and tumor tissue (although limited in number of tumor biopsies) from the same subject is required to help understand and correlate pharmacodynamic events resulting from combined blockade of KIR and ipilimumab and inform potential mechanisms or clinical outcome.

BRAF and EGFR status are also assessed. If the BRAF or EGFR mutation status is known, and there is documentation, no other tumor assessment is performed. If the mutation status is unknown, BRAF or EGFR mutation status may be assessed on archival tumor tissue.

Peripheral Blood Collection:

Blood is drawn. Further details of blood collection and processing are provided to the site in the procedure manual. The pharmacodynamics of lirilumab and ipilimumab combination are assessed by quantifying biomarkers from peripheral blood. For the following Peripheral Blood Assessments blood samples are taken from the first six subjects in doses escalation and for all patients who consent to pre-treatment and on-treatment biopsies (minimum of 10 patients in the melanoma cohort expansion and all others who consent for biopsies).

NK Functional Assays and KIR Receptor Occupancy:

Pre-treatment and on-treatment PBMCs are used to investigate the relationship between KIR (target of lirilumab) occupancy and NK function as measured by CD107a, and intracellular INF-γ expression using flow cytometry in a co-culture assay with surrogate target cells. Specifically, NK cells are isolated from PBMCs and are co-cultured with target cells (HLA class I-positive and HLA class I-negative) in the presence of excess lirilumab to assess the induction of NK cytolytic activity as a function of dose, time after dose, degree of KIR occupancy, and circulating levels of lirilumab (PK). lirilumab occupancy of KIR on NK cells will be monitored using a fluorescently-labeled version of lirilumab. Understanding the relationship between NK function with KIR occupancy and/or circulating lirilumab levels may be important in establishing optimal drug dosage and/or the timing of the evaluation of other biomarkers.

T Cell Functional Assay:

Pre-treatment and on-treatment PBMCs are used to investigate the effects of lirilumab and ipilimumab on T cell function as measured by intracellular INFγ expression using flow cytometry. Specifically, T cell subsets are incubated on anti-CD3-coated plates to assess T cell activation as a function of dose, time after dose, and circulating levels of lirilumab and ipilimumab (PK). Understanding the relationship between T cell activation and various dose combinations of lirilumab and ipilimumab levels may be important to establish optimal drug dosage and/or timing of evaluating other biomarkers.

Immune Response Analysis (Soluble Factors):

Pre-treatment and on-treatment serum levels of chemokines, cytokines and other immune mediators are assessed by techniques that may include, but are not limited to ELISA or multiplex assays. Analytes may include markers of immune activation, modulation, or inflammation such as IFN-γ, soluble NKG2D ligands (i.e., soluble MICA), and sCD25.

T Cell and NK Cell Immunophenotyping:

The relative proportion of lymphocyte subsets are assessed from peripheral blood samples. Additionally, PBMCs are used to characterize and quantitate specific markers of inhibition and activation on NK and T cell subsets by polychromatic flow cytometry. Immunophenotyping of Treg cells may include, but is not limited to: HLA-DR, CD3, CD4, FoxP3, PD-L1, PD-1, LAG-3, ICOS, and CD25. Immunophenotyping of memory/effector T cells may include, but not limited to: CCR7, CD45RA, CD27, CD28, CD3, CD4, CD8, Ki67, HLA-DR, PD-L1, PD-1, CTLA-4, and ICOS. NK immunophenotyping may include, but is not limited to: CD56, CD3, CD16, CD54, CD94, KIR, NKG2D, NKp30, NKp46, IL-21R, Ki67, CD25, and granzyme B.

Total KIR Expression:

An absolute enumeration of KIR-positive expressing cells will be determined from peripheral blood samples collected pre-treatment and at the beginning of maintenance. Flow cytometry will be used to assess not only the percent of positive KIR-expressing cells (KIR2DL1/2/3) but also to quantitate the amount of KIR expression.

KIR and HLA Genotyping:

Blood samples obtained from all subjects in cohort expansion during screening are used to isolate DNA for the determination of KIR and HLA genotype by polymerase chain reaction (PCR). The association between KIR and HLA genotype and clinical outcomes to lirilumab in combination with ipilimumab are evaluated.

12. Adverse Events

An adverse event (AE) is defined as any new untoward medical occurrence or worsening of a preexisting medical condition in a clinical investigation subject administered an investigational (medicinal) product and that does not necessarily have a causal relationship with this treatment. An AE can therefore be any unfavorable and unintended sign (such as an abnormal laboratory finding), symptom, or disease temporally associated with the use of investigational product, whether or not considered related to the investigational product.

The causal relationship to study drug is determined by a physician and should be used to assess all adverse events (AE). The casual relationship can be one of the following:

Related: There is a reasonable causal relationship between study drug administration and the AE.

Not related: There is not a reasonable causal relationship between study drug administration and the AE.

The term "reasonable causal relationship" means there is evidence to suggest a causal relationship.

Adverse events can be spontaneously reported or elicited during open-ended questioning, examination, or evaluation of a subject. (In order to prevent reporting bias, subjects are not questioned regarding the specific occurrence of one or more AEs.)

A serious adverse event (SAE) is any untoward medical occurrence that at any dose:

results in death is life-threatening (defined as an event in which the subject was at risk of death at the time of the event; it does not refer to an event which hypothetically might have caused death if it were more severe)

requires inpatient hospitalization or causes prolongation of existing hospitalization results in persistent or significant disability/incapacity is a congenital anomaly/birth defect is an important medical event (defined as a medical event(s) that may not be immediately life-threatening or result in death or hospitalization but, based upon appropriate medical and scientific judgment, may jeopardize the subject or may require intervention [e.g., medical, surgical] to prevent one of the other serious outcomes listed in the definition above). Examples of such events include, but are not limited to, intensive treatment in an emergency room or at home for allergic bronchospasm; blood dyscrasias or convulsions that do not result in hospitalization). Potential drug induced liver injury (DILI) is also considered an important medical event.

Suspected transmission of an infectious agent (e.g., pathogenic or nonpathogenic) via the study drug is an SAE. Although pregnancy, overdose, cancer, and potential drug induced liver injury (DILI) are not always serious by regulatory definition, these events must be handled as SAEs. Any component of a study endpoint that is considered related to study therapy (e.g., death is an endpoint, if death occurred due to anaphylaxis, anaphylaxis must be report) is reported as an SAE.

The following hospitalizations are not considered SAEs:

a visit to the emergency room or other hospital department <24 hours, that does not result in admission (unless considered an important medical or life-threatening event)

elective surgery, planned prior to signing consent admissions as per protocol for a planned medical/surgical procedure routine health assessment requiring admission for baseline/trending of health status (e.g., routine colonoscopy)

medical/surgical admission other than remedying ill health state and planned prior to entry into the study. Appropriate documentation is required in these cases admission encountered for another life circumstance that carries no bearing on health status and requires no medical/surgical intervention (e.g., lack of housing, economic inadequacy, care-giver respite, family circumstances, administrative).

Following the subject's written consent to participate in the study, all SAEs, whether related or not related to study drug, are collected, including those thought to be associated with protocol-specified procedures. All SAEs that occur during the screening period and within 90 days of discontinuation of dosing are collected. If applicable, SAEs that relate to any later protocol-specified procedure (e.g., a follow-up skin biopsy) are also collected. The investigator reports any SAE occurring after these time periods that is believed to be related to study drug or protocol-specified procedure. An SAE report is completed for any event where doubt exists regarding its status of seriousness.

If the investigator believes that an SAE is not related to study drug, but is potentially related to the conditions of the study (such as withdrawal of previous therapy, or a complication of a study procedure), the relationship is specified in the narrative section of the SAE Report Form.

SAEs, whether related or not related to study drug, and pregnancies are reported within 24 hours. SAEs are recorded on the SAE Report Form; pregnancies on a Pregnancy Surveillance Form (electronic or paper forms).

If only limited information is initially available, follow-up reports are required. (Note: Follow-up SAE reports include the same investigator term(s) initially reported.)

If an ongoing SAE changes in its intensity or relationship to study drug or if new information becomes available, a follow-up SAE report is sent within 24 hours to BMS (or designee) using the same procedure used for transmitting the initial SAE report. All SAEs are followed to resolution or stabilization.

13. Statistical Considerations

Dose Escalation: As this is a Phase 1 dose escalation trial, the sample size at each dose depends on observed toxicity and cannot be determined precisely. Between 6 and 12 subjects are treated during the dose escalation segment (Cohorts 1-5) at each dose. Using a 6+3 design ensures that six subjects at each dose are assessed for a signal on the pharmacodynamic effects of the studied biomarkers.

Cohort Expansion: For dose expansion cohorts, approximately 20 subjects are enrolled in each of 3 tumor types and treated at the previously determined MTD, MAD, or at an alternative dose as determined by the investigators and the sponsor. In an expansion cohort, if 2 (10%), 3 (15%), or 4 (20%) responses are observed, then the lower limit of the 90% one-sided confidence intervals for the objective response rate is 2.7%, 5.6% and 9.0%, respectively. In addition, 5 responses are needed observed in 20 subjects so that the 80% confidence interval is entirely above 10% for the response rate. These calculations are based on the Clopper-Pearson method for exact confidence intervals. In addition, if the true ORR in a tumor type/expansion cohort is 15%, then with 20 patients in each cohort there is 82% chance of observing at least 2 responses, and 60% chance of observing at least 3 responses, and there is 18% chance of observing 0 or 1 response (false negative rate). If the true ORR in a tumor type is 5% rather than 15%, then there is 26% and 8% chance respectively that there will be at least 2 or at least 3 responses in 20 subjects (false positive rate).

Populations for Analyses:

All Enrolled Data set: subjects who signed informed consent and registered in the study.

All Treated Data set: all subjects who received at least one dose of either study drug.

Response-Evaluable Data Set: all treated subjects who receive either study drug, have a baseline tumor assessment with measurable disease, and one of the following:
1) at least one evaluable on-treatment tumor assessment,
2) clinical progression, or
3) death prior to the first on-treatment tumor evaluation.

Lirilumab Pharmacokinetic Data Set: all subjects who receive lirilumab and have adequate serum concentration data for lirilumab PK.

Ipilimumab Pharmacokinetic Data Set: all subjects who receive ipilimumab and have adequate ipilimumab PK.

Lirilumab Immunogenicity Data Set: all subjects who receive at least one dose of lirilumab and have at least one ADA sample available.

Ipilimumab Immunogenicity Data Set: all subjects who receive at least one dose of ipilimumab and have at least one ADA sample available.

Biomarker Data Set: all treated subjects who have biomarker data available.

Endpoint Definitions: Safety is the primary endpoint of this Phase 1 study. All subjects who receive study drug therapy are evaluated for safety as measured by the rate of adverse events (AEs), and serious adverse events (SAEs), and are assessed during treatment and for 90 days in follow-up. This objective is measured by the following endpoints:
a) Incidence of adverse events: all non-serious adverse events are collected from Day 1 until 90 days after the subject's last dose of study drug or until they discontinue the study. All serious adverse events must be collected from the date of the subject's written consent until 90 days after discontinuation of dosing or until they discontinue the study.
b) Incidence of clinical laboratory test abnormalities including hematology and serum chemistry, and thyroid panel abnormalities assessed at specified time points.

Assessments are based on adverse event reports and the results of vital sign measurements, electrocardiograms (ECGs), physical examinations, imaging studies, and clinical laboratory tests. Adverse events are categorized using the most current version of the Medical Dictionary for Regulatory Activities (MedDRA); both AEs and laboratory tests will be graded using National Cancer Institute (NCI) Common Terminology Criteria for Adverse Events (CTCAE) v4.

The secondary objective of assessing preliminary anti-tumor activity is based on endpoints described using irRECIST (Wolchok J D, et al., *Clin Cancer Res* 2009; 15:7412-7420) and RECIST v1.1 (Eisenhauer E A, *Eur J Cancer* 2009; 45:228-247). For the purposes of patient management, clinical decision making is based exclusively on irRECIST. Therefore timepoint tumor response evaluations is recorded on the CRF based on investigators' assessments using irRECIST criteria. Statistical analysis and reporting are based on both criteria.

Best overall response (BOR) is the best response designation recorded from the start of the study treatment until the end of treatment taking into account any requirement for confirmation, based on RECIST v1.1 or irRECIST criteria. CR or PR determinations included in the BOR assessment are confirmed by a consecutive second (confirmatory) evaluation meeting the criteria for response that is performed at least 4 weeks after the criteria for response are first met.

Objective response rate (ORR) is defined as the total number of subjects whose BOR is either CR or PR divided by the total number of subjects in the population of interest.

Duration of Response (DOR) computed only for subjects with a BOR of CR or PR is defined as the number of days between the date of first response and the subsequent date of objectively documented disease progression based on the criteria (RECIST v1.1 or irRECIST) or death, whichever occurs first. For those subjects who remain alive and have not progressed or received subsequent therapy, duration of response is censored on the date of last tumor assessment. Subjects who receive subsequent therapy are censored at the start of subsequent therapy.

Progression-Free Survival Rate (PFSR) is defined as the probability of a subject remaining progression-free and surviving to 24 weeks. The probability is computed based on the number of days between the first dose of study drug and progressive disease or death, as defined by each criterion. For those subjects who remain alive and have not progressed, PFS is censored on the date of the last tumor assessment. The above is calculated based on tumor measurements occurring every 6 weeks until maintenance treatment and then every 12 weeks or until confirmed disease progression and/or follow-up. Overall survival is an exploratory efficacy endpoint.

Pharmacokinetics (PK): Lirilumab maximum concentration Cmax (μg/mL), time to maximum concentration Tmax (hr), Area under the curve AUCTAU (μg.hr/mL), Area under the curve AUCinf (μg.hr/mL), Clearance (L/day), Volume of distribution (Vss (L)), half-life (t½ days), and trough concentration Cmin (μg/mL) are evaluated using non-compartmental analysis in all study subjects Pharmacokinetics of ipilimumab: PK is measured to derive the end of infusion and trough (Cmin) concentration at specified visits.

Immunogenicity: Occurrence of specific ADA to lirilumab and ipilimumab when co-administered is determined.

Biomarkers: Measures of TILs, PD-L1 and HLA Class I expression using immunohistochemistry on mandatory tumor biopsies from a minimum of ten melanoma subjects in cohort expansion, including baseline and changes from baseline outcomes.

Exploratory Endpoints: Biomarkers from peripheral blood include measures of KIR and HLA genotypes, KIR occupancy, NK and T cell functional assays, soluble factors, KIR expression on NK cells. Overall Survival (OS) is an exploratory efficacy endpoint.

14. Analyses

Demographics and Baseline Characteristics: Frequency distributions of gender and race are tabulated. Summary statistics for age, body weight, and height are collected, and Body Mass Index (BMI) is derived.

Efficacy Analyses: Individual best overall response (BOR), duration of response and PFS are listed using RECIST v1.1 and irRECIST criteria. BOR outcomes are tabulated by disease type and dose. The objective response rate (ORR) and PFS rate (e.g. at 24 weeks) and corresponding confidence interval are provided by tumor type and treatment. The duration of response, duration of stable disease and PFS are estimated by Kaplan-Meier methodology by disease type, depending on data availability. PFS rates at 24 weeks are similarly estimated, based on K-M methodology. ORR, duration of response and PFS analyses include subjects in the cohort expansion phase and subjects in dose escalation matching those in cohort expansion by disease type and treatment. Individual changes in the tumor burden over time are presented graphically within a disease type. Landmark overall survival is assessed as part of exploratory efficacy analysis, by Kaplan-Meier plots and medians for each tumor type.

Safety Analyses: All recorded adverse events are listed and tabulated by system organ class, preferred term and treatment. Vital signs and clinical laboratory test results are listed and summarized by treatment. Any significant physical examination findings, and clinical laboratory results are listed. ECG readings are evaluated by the investigator and abnormalities, if present, are listed.

Pharmacokinetic Analyses: Summary statistics are tabulated for the pharmacokinetic parameters of lirilumab by dose and study day/week. To describe the dependency on dose of anti-KIR, scatter plots of Cmax and AUC(TAU) versus dose are provided for each day measured. Dose proportionality of lirilumab when co-administered with ipilimumab is assessed based on a power model. Ipilimumab end of infusion and trough (Cmin) concentration is tabulated by summary statistics. These data are also pooled with other datasets for population PK analysis which is part of a separate report.

Biomarker Analyses: The pharmacodynamic effect of lirilumab on Tumor Infiltrating Lymphocytes (TILs) and expression of tumor markers including PD-L1 and HLA Class I are assessed by summary statistics, and investigated graphically to explore patterns of change, e.g., with drug exposure, for subjects in the melanoma expansion cohort. In addition, the correlation of TIL changes and tumor antigen expression with measures of peripheral blood markers is explored graphically, or by appropriate statistical methods based on data availability, for assessing associations.

Exploratory Biomarker Analyses: The pharmacodynamic effect of lirilumab on KR occupancy and the combination of ipilimumab given with lirilumab on markers in peripheral blood and serum proteins is assessed by summary statistics, and investigated graphically to explore patterns of change over time, and how the patterns differ among dose levels and exposure. If there is a meaningful indication in the pattern over time, further analysis (e.g., by linear mixed model) is performed to characterize the relationship. Pharmacodynamic effects on tumor markers in cohorts other than melanoma are similarly assessed depending on data availability. Associations between biomarker measures from peripheral blood or tumor biopsy and clinical outcomes are also explored graphically, and further assessed as needed by methods such as, but not limited to logistic regression, and characterized by appropriate statistics.

Other Analyses: A listing is provided of all available immunogenicity data. Additionally, a listing of immunogenicity data from those subjects with at least one positive anti-drug antibody (ADA) at any time point is provided by treatment for each analyte. The frequency of subjects with at least one positive ADA assessment and frequency of subjects who develop ADA after a negative baseline assessment are provided. To examine the potential relationship between immunogenicity and safety, the frequency and type of AEs of special interest are examined by overall immunogenicity status. Associations between trough concentrations of lirilumab (or ipilimumab) and corresponding ADA assessments are explored.

Interim Analyses: Data emerging from each panel of this exploratory study are needed for timely decisions about adjustments to procedures in subsequent parts of the study. Therefore, data are reviewed prior to the final lock of the study database. Additional interim analyses are also performed for administrative purposes or publications. Analyses only consist of listings, summaries, and graphs of the available data. No formal inferences requiring any adjustment to statistical significance level are performed. Efficacy analyses based on interim data use response evaluable or all treated populations depending on the purpose of the analysis.

SEQUENCE SUMMARY

| SEQ ID NO: | SEQUENCE |
|---|---|
| 1 | Heavy Chain Amino Acid Sequence Anti-KIR mAb (IPH2102/Lirilumab) (CDRs underlined) QVQLVQSGAE VKKPGSSVKV SCKASGGTFS FYAISWVRQA PGQGLEWMGG FIPIFGAANY AQKFQGRVTI TADESTSTAY MELSSLRSDD TAVYYCARIP |

| SEQ ID NO: | SEQUENCE |
|---|---|
| | SGSYYYDYDM DVWGQGTTVT VSSASTKGPS VFPLAPCSRS TSESTAALGC<br>LVKDYFPEPV TVSWNSGALT SGVHTFPAVL QSSGLYSLSS VVTVPSSSLG<br>TKTYTCNVDH KPSNTKVDKR VESKYGPPCP PCPAPEFLGG PSVFLFPPKP<br>KDTLMISRTP EVTCVVVDVS QEDPEVQFNW YVDGVEVHNA KTKPREEQFN<br>STYRVVSVLT VLHQDWLNGK EYKCKVSNKG LPSSIEKTIS KAKGQPREPQ<br>VYTLPPSQEE MTKNQVSLTC LVKGFYPSDI AVEWESNGQP ENNYKTTPPV<br>LDSDGSFFLY SRLTVDKSRW QEGNVFSCSV MHEALHNHYT QKSLSLSLGK |
| 2 | Light Chain Amino Acid Sequence<br>Anti-KIR mAb (IPH2102/Lirilumab)<br>(CDRs underlined)<br>EIVLTQSPVT LSLSPGERAT LSCRASQSVS SYLAWYQQKP GQAPRLLIYD<br>ASNRATGIPA RFSGSGSGTD FTLTISSLEP EDFAVYYCQQ RSNWMYTFGQ<br>GTKLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC |
| 3 | Heavy Chain Variable Region (VH) Amino Acid Sequence<br>Anti-KIR mAb (IPH2102/Lirilumab) - (SEQ ID NO: 17 from<br>WO 2006/003179)<br>QVQLVQSGAEVKKPGSSVKVSCKASGGTFSFYAISWVRQAPGQGLEWMGGFIPIF<br>GAANYAQKFQGRVTITADESTSTAYMELSSLRSDDTAVYYCARIPSGSYYYDYDMD<br>VWGQGTTVTVSS |
| 4 | Heavy Chain Variable Region (VH) Nucleotide Sequence<br>Anti-KIR mAb (IPH2102/Lirilumab) - (SEQ ID NO: 18 from<br>WO 2006/003179)<br>caggtccagc tggtgcagtc tggggctgag gtgaagaagc ctggggtcctc<br>ggtgaaggtc tcctgcaagg cttctggagg caccttcagt ttctatgcta<br>tcagctgggt gcgacaggcc cctggacaag gcttgagtg gatgggaggg<br>ttcatcccta tctttggtgc agcaaactac gcacagaagt tccagggcag<br>agtcacgatt accgcggacg aatccacgag cacagcctac atggaactga<br>gcagcctgag atctgacgac acggccgtgt attactgtgc gagaatccct<br>agtgggagct actactacga ctacgatatg gacgtctggg gccaagggac<br>cacggtcacc gtctcctca |
| 5 | Light Chain Variable Region (VL) Amino Acid Sequence<br>Anti-KIR mAb (IPH2102/Lirilumab) - (SEQ ID NO: 15 from<br>WO 2006/003179)<br>EIVLTQSPVTLSLSPGERATLSCRASQSVSSYLAWYQQKPGQAPRLLIYD<br>ASNRATGIPARFSGSGSGTDFTLTISSLEPEDFAVYYCQQRSNWMYTFGQ<br>GTKLEIKRT |
| 6 | Light Chain Variable Region (VL) Nucleotide Sequence<br>Anti-KIR mAb (IPH2102/Lirilumab) - (SEQ ID NO: 16 from<br>WO 2006/003179)<br>gaaattgtgt tgacacagtc tccagtcacc ctgtctttgt ctccagggga<br>aagagccacc ctctcctgca gggccagtca gagtgttagc agctacttag<br>cctggtacca acagaaacct ggccaggctc ccaggctcct catctatgat<br>gcatccaaca gggccactgg catcccagcc aggttcagtg gcagtgggtc<br>tgggacagac ttcactctca ccatcagcag cctagagcct gaagattttg<br>cagtttatta ttgtcagcag cgtagcaact ggatgtacac ttttggccag<br>gggaccaagc tggagatcaa acgaact |
| 7 | Heavy Chain CDR1 Amino Acid Sequence<br>Anti-KIR mAb (IPH2102/Lirilumab) - (from Figure 15 of<br>WO 2006/003179)<br>(corresponds to amino acid residues 31-35 of SEQ ID NO: 1)<br>FYAIS |
| 8 | Heavy Chain CDR2 Amino Acid Sequence<br>Anti-KIR mAb (IPH2102/Lirilumab) - (from Figure 15 from<br>WO 2006/003179)<br>(corresponds to amino acid residues 50-65 of SEQ ID NO: 1)<br>GFIPIFGAANYAQKFQ |
| 9 | Heavy Chain CDR3 Amino Acid Sequence<br>Anti-KIR mAb (IPH2102/Lirilumab) - (from Figure 15 from<br>WO 2006/003179)<br>(corresponds to amino acid residues 99-112 of SEQ ID NO: 1)<br>IPSGSYYYDYDMDV |

SEQUENCE SUMMARY

| SEQ ID NO: | SEQUENCE |
|---|---|
| 10 | Light Chain CDR1 Amino Acid Sequence<br>Anti-KIR mAb (IPH2102/Lirilumab) - (from Figure 15 from WO 2006/003179)<br>(corresponds to amino acid residues 24-34 of SEQ ID NO: 3)<br>RASQSVSSYLA |
| 11 | Light Chain CDR2 Amino Acid Sequence<br>Anti-KIR mAb (IPH2102/Lirilumab) - (from Figure 15 from WO 2006/003179)<br>(corresponds to amino acid residues 50-56 of SEQ ID NO: 3)<br>DASNRAT |
| 12 | Light Chain CDR3 Amino Acid Sequence<br>Anti-KIR mAb (IPH2102/Lirilumab) - (from Figure 15 from WO 2006/003179)<br>(corresponds to amino acid residues 89-97 of SEQ ID NO: 3)<br>QQRSNWMYT |
| 13 | KIR2DL1 Extracellular Domain<br>(SEQ ID NO: 23 from WO 2006/003179)<br>HEGVHRKPSLLAHPGXLVKSEETVILQCWSDVMFEHFLLHREGMFNDT<br>LRLIGEHHDGVSKANFSISRMTQDLAGTYRCYGSVTHSPYQVSAPSDPLD<br>IVIIGLYEKPSLSAQXGPTVLAGENVTLSCSSRSSYDMYHLSREGEAHER<br>RLPAGPKVNGTFQADFPLGPATHGGTYRCFGSFHDSPYEWSKSSDPLLVS<br>VTGNPSNSWPSPTEPSSKTGNPRHLH |
| 14 | KIR2DL2 Extracellular Domain<br>(SEQ ID NO: 24 from WO 2006/003179)<br>HEGVHRKPSLLAHPGRLVKSEETVILQCWSDVRFEHFLLHREGKFKDTLH<br>LIGEHHDGVSKANFSIGPMMQDLAGTYRCYGSVTHSPYQLSAPSDPLDIV<br>ITGLYEKPSLSAQPGPTVLAGESVTLSCSSRSSYDMYHLSREGEAHECRF<br>SAGPKVNGTFQADFPLGPATHGGTYRCFGSFRDSPYEWSNSSDPLLVSVI<br>GNPSNSWPSPTEPSSKTGNPRHLH |
| 15 | KIR2DL3 Extracellular Domain<br>(SEQ ID NO: 25 from WO 2006/003179)<br>HEGVHRKPSLLAHPGPLVKSEETVILQCWSDVRFQHFLLHREGKFKDTLH<br>LIGEHHDGVSKANFSIGPMMQDLAGTYRCYGSVTHSPYQLSAPSDPLDIV<br>ITGLYEKPSLSAQPGPTVLAGESVTLSCSSRSSYDMYHLSREGEAHERRF<br>SAGPKVNGTFQADFPLGPATHGGTYRCFGSFRDSPYEWSNSSDPLLVSVT<br>GNPSNSWPSPTEPSSETGNPRHLH |
| 16 | KIR2DS4 Extracellular Domain<br>(SEQ ID NO: 38 from WO 2006/003179)<br>QEGVHRKPSFLALPGHLVKSEETVILQCWSDVMFEHFLLHREGKFNNTLH<br>LIGEHHDGVSKANFSIGPMMPVLAGTYRCYGSVPHSPYQLSAPSDPLDMV |
| 17 | Heavy Chain Amino Acid Sequence<br>Anti-CTLA-4 mAb (Ipilimumab)<br>(variable region underlined; constant region bold)<br><u>QVQLVESGGGVVQPGRSLRLSCAASGFTFSSYTMHWV</u><br><u>RQAPGKGLEWVTFISYDGNNKYYADSVKGRFTISRDNS</u><br><u>KNTLYLQMNSLRAEDTAIYYCARTGWLGPFDYWGQGT</u><br><u>LVTVSS</u>ASTKGPSVFPLAPSSKSTSGGTAALGCLVKDYFP<br>EPVTVSWNSGALTSGVHTFPAVLQSSGLYSLSSVVTVPS<br>SSLGTQTYICNVNHKPSNTKVDKRVEPKSCDKTHTCPPC<br>PAPELLGGPSVFLFPPKPKDTLMISRTPEVTCVVVDVSHE<br>DPEVKFNWYVDGVEVHNAKTKPREEQYNSTYRVVSVLT<br>VLHQDWLNGKEYKCKVSNKALPAPIEKTISKAKGQPREP<br>QVYTLPPSRDELTKNQVSLTCLVKGFYPSDIAVEWESNG<br>QPENNYKTTPPVLDSDGSFFLYSKLTVDKSRWQQGNVF<br>SCSVMHEALHNHYTQKSLSLSPGK |
| 18 | Light Chain Amino Acid Sequence<br>Anti-CTLA-4 mAb (Ipilimumab)<br>(variable region underlined; constant region bold)<br><u>EIVLTQSPGTLSLSPGERATLSCRASQSVGSSYLAWYQQ</u><br><u>KPGQAPRLLIYGAFSRATGIPDRFSGSGSGTDFTLTISRL</u><br><u>EPEDFAVYYCQQYGSSPWTFGQGTKVEIK</u>RTVAAPSV<br>FIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC |

SEQUENCE SUMMARY

| SEQ ID NO: | SEQUENCE |
| --- | --- |
| 19 | Heavy Chain Variable Region (VH) Amino Acid Sequence Anti-CTLA-4 mAb (Ipilimumab) - (SEQ ID NO: 6 of US 8,119,129)<br>QVQLVESGGGVVQPGRSLRLSCAASGFTFSSYTMHWVRQAPGKGLEWVTF<br>ISYDGNNKYYADSVKGRFTISRDNSKNTLYLQMNSLRAEDTAIYYCART<br>GWLGPFDYWGQGTLVTVSS |
| 20 | Light Chain Variable Region (VL) Amino Acid Sequence Anti-CTLA-4 mAb (Ipilimumab) - (SEQ ID NO: 5 of US 8,119,129)<br>EIVLTQSPGTLSLSPGERATLSCRASQSVGSSYLAWYQQKPGQAPRLLI<br>YGAFSRATGIPDRFSGSGSGTDFTLTISRLEPEDFAVYYCQQYGSSPWTF<br>GQGTKVEIK |
| 21 | Heavy Chain CDR1 Amino Acid Sequence Anti-CTLA-4 mAb (Ipilimumab)<br>SYTMH |
| 22 | Heavy Chain CDR2 Amino Acid Sequence Anti-CTLA-4 mAb (Ipilimumab)<br>FISYDGNNKYYADSVKG |
| 23 | Heavy Chain CDR3 Amino Acid Sequence Anti-CTLA-4 mAb (Ipilimumab)<br>TGWLGPFDY |
| 24 | Light Chain CDR1 Amino Acid Sequence Anti-CTLA-4 mAb (Ipilimumab)<br>RASQSVGSSYLA |
| 25 | Light Chain CDR2 Amino Acid Sequence Anti-CTLA-4 mAb (Ipilimumab)<br>GAFSRAT |
| 26 | Light Chain CDR3 Amino Acid Sequence Anti-CTLA-4 mAb (Ipilimumab)<br>QQYGSSPWT |
| 27 | Human CTLA-4 Sequence (GenBank: AAL07473.1)<br>MACLGFQRHK AQLNLATRTW PCTLLFFLLF IPVFCKAMHV AQPAVVLASS<br>RGIASFVCEY ASPGKATEVR VTVLRQADSQ VTEVCAATYM MGNELTFLDD<br>SICTGTSSGN QVNLTIQGLR AMDTGLYICK VELMYPPPYY LGIGNGTQIY<br>VIDPEPCPDS DFLLWILAAV SSGLFFYSFL LTAVSLSKML KKRSPLTTGV<br>YVKMPPTEPE CEKQFQPYFI PIN |

What is claimed is:

1. A method of treating a solid tumor in a human patient diagnosed with non-small cell lung cancer (NSCLC), castrate resistant prostate cancer (CRPC) and/or melanoma, the method comprising: administering to the patient an effective amount of each of:
    (a) an anti-KIR antibody comprising the CDR1, CDR2 and CDR3 domains in a heavy chain variable region having the sequences set forth in SEQ ID NO:3, and the CDR1, CDR2 and CDR3 domains in a light chain variable region having the sequences set forth in SEQ ID NO:5 and
    (b) an anti-CTLA-4 antibody comprising the CDR1, CDR2 and CDR3 domains in a heavy chain variable region having the sequences set forth in SEQ ID NO:19, and the CDR1, CDR2 and CDR3 domains in a light chain variable region having the sequences set forth in SEQ ID NO:20,
    wherein the anti-KIR antibody and anti-CTLA-4 antibody are administered in combination (A) every 3 weeks for a total of 4 doses over 12 weeks during an induction phase, followed by (B) every 12 weeks for 4 doses starting at week 24 during a maintenance phase, and
    wherein the anti-KIR antibody is administered at a dose of 0.1, 0.3, 1, 3 or 10 mg/kg, and the anti-CTLA-4 antibody is administered at a dose of 3 or 10 mg/kg during both phases.

2. The method of claim 1, wherein the anti-KIR antibody and anti-CTLA-4 antibody are administered at the following doses during either the induction or maintenance phase:
    (a) 0.1 mg/kg anti-KIR antibody and 3 mg/kg of anti-CTLA-4 antibody;
    (b) 0.3 mg/kg anti-KIR antibody and 3 mg/kg of anti-CTLA-4 antibody;
    (c) 1 mg/kg anti-KIR antibody and 3 mg/kg of anti-CTLA-4 antibody;
    (d) 3 mg/kg anti-KIR antibody and 3 mg/kg of anti-CTLA-4 antibody;
    (e) 10 mg/kg anti-KIR antibody and 3 mg/kg of anti-CTLA-4 antibody;
    (f) 3 mg/kg anti-KIR antibody and 10 mg/kg of anti-CTLA-4 antibody; or
    (g) 10 mg/kg anti-KIR antibody and 10 mg/kg of anti-CTLA-4 antibody.

3. The method of claim 1, wherein the anti-KIR and anti-CTLA-4 antibodies are formulated for intravenous administration.

4. The method of claim 1, wherein the anti-KIR and anti-CTLA-4 antibodies are administered on (1) day 1, week 1, (2) day 22, week 4, (3) day 43, week 7, and (4) day 64, week 10 of the induction phase.

5. The method of claim 1, wherein the induction phase ends on day 84 of week 12.

6. The method of claim 1, wherein the anti-KIR and anti-CTLA-4 antibodies are administered on day 1 of week 24, day 1 of week 36, day 1 of week 48, and day 1 of week 60 of the maintenance phase.

7. The method of claim 1, wherein the anti-KIR and anti-CTLA-4 antibodies are administered simultaneously.

8. The method of claim 1, wherein the anti-CTLA-4 antibody is administered before or after administration of the anti-KIR antibody.

9. The method of claim 1, wherein the treatment produces at least one therapeutic effect chosen from a reduction in size of a tumor, reduction in number of metastasic lesions over time, complete response, partial response, and stable disease.

10. The method of claim 1, wherein the anti-KIR antibody comprises
    (a) a heavy chain variable region CDR1 having the sequence set forth in SEQ ID NO:7;
    (b) a heavy chain variable region CDR2 having the sequence set forth in SEQ ID NO:8;
    (c) a heavy chain variable region CDR3 having the sequence set forth in SEQ ID NO:9;
    (d) a light chain variable region CDR1 having the sequence set forth in SEQ ID NO:10;
    (e) a light chain variable region CDR2 having the sequence set forth in SEQ ID NO:11; and
    (f) a light chain variable region CDR3 having the sequence set forth in SEQ ID NO:12.

11. The method of claim 1, wherein the anti-KIR antibody comprises heavy and light chain variable regions having the sequences set forth in SEQ ID NOs:3 and 5, respectively.

12. The method of claim 1, wherein the anti-KIR antibody comprises heavy and light chains having the sequences set forth in SEQ ID NOs:1 and 2, respectively.

13. The method of claim 1, wherein the anti-CTLA-4 antibody comprises
    (a) a heavy chain variable region CDR1 having the sequence set forth in SEQ ID NO:21;
    (b) a heavy chain variable region CDR2 having the sequence set forth in SEQ ID NO:22;
    (c) a heavy chain variable region CDR3 having the sequence set forth in SEQ ID NO:23;
    (d) a light chain variable region CDR1 having the sequence set forth in SEQ ID NO:24;
    (e) a light chain variable region CDR2 having the sequence set forth in SEQ ID NO:25; and
    (f) a light chain variable region CDR3 having the sequence set forth in SEQ ID NO:26.

14. The method of claim 1, wherein the anti-CTLA-4 antibody comprises heavy and light chain variable regions having the sequences set forth in SEQ ID NOs:19 and 20, respectively.

15. The method of claim 1, wherein the anti-CTLA-4 antibody comprises heavy and light chains having the sequences set forth in SEQ ID NOs:17 and 18, respectively.

* * * * *